(12) United States Patent
Daley et al.

(10) Patent No.: US 9,326,971 B2
(45) Date of Patent: May 3, 2016

(54) 4-METHYLPYRAZOLE FORMULATIONS FOR INHIBITING ETHANOL INTOLERANCE

(71) Applicant: Raptor Pharmaceuticals Inc., Novato, CA (US)

(72) Inventors: Thomas E. Daley, San Mateo, CA (US); Elizabeth C. Squiers, Half Moon Bay, CA (US); Kin-Hung Peony Yu, Hillsborough, CA (US)

(73) Assignee: RAPTOR PHARMACEUTICALS INC., Novato, CA (US)

( * ) Notice: Subject to any disclaimer, the term of this patent is extended or adjusted under 35 U.S.C. 154(b) by 0 days.

(21) Appl. No.: 14/173,088

(22) Filed: Feb. 5, 2014

(65) Prior Publication Data

US 2014/0155450 A1 Jun. 5, 2014

Related U.S. Application Data

(63) Continuation of application No. 13/757,329, filed on Feb. 1, 2013, now abandoned, which is a continuation of application No. 12/797,594, filed on Jun. 9, 2010, now abandoned, and a continuation-in-part of application No. 10/591,735, filed as application No. PCT/US2005/007273 on Mar. 3, 2005, now abandoned.

(60) Provisional application No. 61/185,884, filed on Jun. 10, 2009, provisional application No. 60/642,007, filed on Jan. 6, 2005, provisional application No. 60/550,261, filed on Mar. 3, 2004.

(51) Int. Cl.
*A61K 31/415* (2006.01)

(52) U.S. Cl.
CPC .................................. *A61K 31/415* (2013.01)

(58) Field of Classification Search
CPC .................................................. A61K 31/415
See application file for complete search history.

(56) References Cited

U.S. PATENT DOCUMENTS

| 6,120,806 A | 9/2000 | Whitmire |
| 2005/0069587 A1 | 3/2005 | Modi et al. |
| 2005/0147565 A1 | 7/2005 | Sequeira et al. |
| 2008/0021083 A1 | 1/2008 | Daley |
| 2009/0117079 A1 | 5/2009 | Monte |

FOREIGN PATENT DOCUMENTS

JP S57-106620 U 7/1982

OTHER PUBLICATIONS

Blomstrand et al., Inhibitory Effect on Ethanol Oxidation in Man After Administration of 4-Methylpyrazole, *Life Sciences*, 9:631-40 (1970).
Bosron et al., Genetic Polymorphism of Human Liver Alcohol and Aldehyde Dehydrogenases, and their Relationship to Alcohol Metabolism and Alcoholism, *Hepatology*, 6(3):502-10 91986).
Casavant et al., Fomepizol in the Treatment of Poisoning, *Pediatrics*, 107 (2001).
Chao et al., Polymorphism of Alcohol and Aldehyde Genes and Alcoholic Cirrhosis in Chinese Patients, *Hepatology*, 19:360-6 (1994).
Chen et al., Interaction between the Functional Polymorphisms of the Alcohol-Metabolism Genes in Protection against Alcoholism, *American Journal of Human Genetics*, 65(3):795-807 (1999).
Crabb et al., Genotypes for Aldehyde Dehydrogenase Deficiency and Alcohol Sensitivity, *Journal of Clinical Investigation*, 83:314-6 (1989).
Crabb et al., Overview of the Role of Alcohol Dehydrogenase and Aldehyde Dehydrogenase and their Variants in the Genesis of Alcohol-Related Pathology, *Proceedings of the Nutrition Society*, 63(1):49-63 (2004).
Enomoto et al., Alcoholic Liver Disease in Heterozygotes of Mutant and Normal Aldehyde Dehdrogenase-2 Genes, *Hepatology*, 13(6):1071-5 (1991).
Enomoto et al., Genenotyping of the Aldehyde Dehydrogenase 2 (ALDH2) Gene using the Polymerase Chain Reaction: Evidence for Single Point Mutation in the ALDH2 Gene of ALDH2-deficiency, *Journal of Gastroenterology*, 26(4):440-7 (1991).
Feierman et al., Increased Sensitivity of the Microsomal Oxidation of Ethanol to Inhibition by Pyrazole and 4-Methylpyrazole after Chronic Ethanol Treatment, *Biochemical Pharmacology*, 36(19):3277-83 (1987).
Goedde et al., Distribution of ADH2 and ALDH2 genotypes in different populations, *Human Genetics*, 88:344-6 (1992).
Inoue et al., Accumulation of Acetaldehyde in Alcohol-Sensitive Japanese: Relation to Ethanol and Acetaldehyde Oxidizing Capacity, *Alcoholism: Clinical and Experimental Research*, 8(3):319-22 (1984).
Inoue et al., Suppression of Acetaldehyde Accumulation by 4-Methylpyrazole in Alcohol-I hypersensitive Japanese, *Japanese Journal of Pharmacology*, 38:43-8 (1985).
ISA/US, International Search Report, dated Aug. 3, 2010, for International Application No. PCT/US10/37879.
ISA/US, International Search Report, dated Mar. 2, 2011, for International Application No. PCT/US10/59065.
ISA/US, Written Opinion, dated Aug. 3, 2010, for International Application No. PCT/US10/37879.
ISA/US, Written Opinion, dated Mar. 2, 2011, for International Application No. PCT/US10/59065.
Jacobsen ct al., 4-Methylpyrazole: A Controlled Study of Safety in Healthy Human Subjects after Single, Ascending Doses, *Alcoholism: Clinical and Experimental Research*, 12:516-22 (1988).
Jacobsen et al., Kinetic Interactions Between 4-Methylpyrazole and Ethanol in Healthy Humans, *Alcoholism: Clinical and Experimental Research*, 20(5):804-9 (1996).

(Continued)

*Primary Examiner* — Paul Zarek
(74) *Attorney, Agent, or Firm* — Marshall, Gerstein & Borun LLP

(57) ABSTRACT

Provided herein are methods, compositions and formulations to prevent or ameliorate ethanol intolerance, reduce or ameliorate symptoms associated with acetaldehyde accumulation accompanying ethanol consumption, or reduce the risk of diseases or disorders caused by acetaldehyde accumulation, comprising administering 4-MP, or physiologically acceptable salts thereof, to subjects with reduced or absent aldehyde dehydrogenase subtype 2 (ALDH2) activity.

15 Claims, 5 Drawing Sheets

(56) References Cited

OTHER PUBLICATIONS

Figure 1:
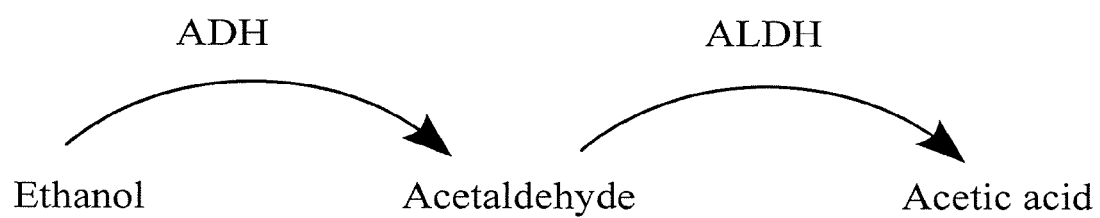

Lindros et al., A Simple Procedure Using 4-Methylpyrazole for Developing Tolerance and other Chronic Alcohol Effects, *Alcohol*, 1(2):145-50 (1984).

Lindros et al., The Disulfiram (Antabuse)-Alcohol Reaction in Male Alcoholics: Its Efficient Management by 4-Methylpyrazole, *Alcoholism: Clinical and Experimental Research*, 5(4):528-30 (1981).

Matsuo et al.. A Gene-Gene Interaction between ALDH2 Glu487Lys and ADH2 His47Arg Polymorphisms Regarding the Risk of Colorectal Cancer in Japan, *Carcinogenesis*, 27(5):1018-23 (2006).

McCarver-May et al., An Accurate. Automated, Simultaneous Gas Chromatographic Headspace Measurement of Whole Blood Ethanol and Acetaldehyde for Human In Vivo Studies, *Journal of Analytical Toxicology*, 21 ( 2):134-41 (1997).

Nagy et al., Atmospheric Pressure Chemical Ionization Mass Spectrometry of Aldehydes in Biological Matrices, *Rapid Communications in Mass Spectrometry*, 18:2473-8 (2004).

Nishiyori ct al., Single-Strand Conformation Polymorphism Analysis for Alcohol Dehydrogenase 2 (ADH2) Genotyping Using Nail Clippings, *Clinical Chemistry*, 48:563-4 (2000).

Ohira et al., Hepatocellular Carcinoma Associated with Alcoholic Liver Disease: A Clinicopathological Study and Genetic Polymorphism of Aldehyde Dehyrogenase 2, *Alcoholism: Clinical and Experimental Research*, 20(3):378a-82a (1996).

Ohsawa et al.. Genetic Deficiency of a Mitochondrial Aldehyde Dehydrogenase Increases Serum Lipid Peroxides in Community-Dwelling Females, *Journal of Human Genetics*, 48:404-9. (2003).

Rydberg et al., 4-Methylpyrozole as an Inhibitor of Ethanol Metabolism: Differential Metabolic and Central Nervous Effects, *Acta pharmacology et toxicology*, 31:421-32 (1972).

Sarkola et al., Ethanol. Acetaldehyde, Acetate, and Lactate Levels After Alcohol Intake in White Men and Women: Effects of 4-Methylpyrazole, *Alcoholism: Clinical and Experimental Research*, 26(2):239-45 (2002).

Scalley et al., Treatment of Ethylene Glycol Poisoning, American Family Physician, 66:807-12 (2002).

Stowell,—An Improved Method for the Determination of Acetaldehyde in Human Blood with Minimal Ethanol Interference, *Clinica Chimica Acta*, 98:201-5 (1979).

Takada et al., Genotypes of ALDH2 Related to Liver and Pulmonary Diseases and Other Genetic Factors Related to Alcoholic Liver Disease, *Alcohol,*. 29(6):719-27 (1994).

Takashita et al., Relationship netween Alcohol Drinking. ADII2 and ALDH2 Genotypes, and Risks for Hepatocellular Carcinoma in Japanese, *Cancer Letters,*. 149:69-76 (2000).

Tamakosiii et al., Duplex Plymerase Chain Reaction with Confronting Two-pair Primers (PCR-CTTP) for Genotyping Alcohol Dehdrogenase13 Subunit (ADH2) and Aldehyde Dehydrogenase 2 (ALDH2), *Alcohol*, 23(5):407-10 (2003).

Truett et al., Preparation of PCR-Quality Mouse Genomic DNA with Hot Sodium Hydroxide and Tris (HotSHOT), *Biotechniques*, 29(1):52-4 (2000).

United States Patent and Trademark Office, Final Office Action for U.S. Appl. No. 13/529,695, (May 13, 2013).

United States Patent and Trademark Office, Non-Final Office Action for U.S. Appl. No. 13/529,695, (Nov. 20, 2012).

Vakevainen et al., 4-Methylpyrazole Decreases Salivary Acetaldehyde Levels in ALDH2-Deficient Subjects but Not in Subjects with Normal ALDH2, *Alcoholism: Clinical and Experimental Research*, 25(6):829-34 (2001).

Visapaa et al., Increased Cancer Risk in Heavy Drinkers with the Alcohol Dehydrogenase 1C*1 Allele, Possibly Due to Salivary Acetaldehyde, *Gut*, 53:871-6 (2004).

Wall et al., Alcohol Metabolism in Asian-American Men with Genetic Polymorphisms of Aldehyde Dehydrogenase, *Annals of Internal Medicine*, 127(5):376-9 (1997).

Ward et al., Identification and Characterisation of Alcohol-Induced Flushing in Caucasian Subjects, *Alcohol and Alcoholism*, 29(4):433-8 (1994).

Wilkin et al.,—4-Methylpyrazole and the Cutaneous Vascular Sensitivity to Alcohol in Orientals, *Journal of Investigative Dermatology*, 91:117-9 (1988).

Xiao et al., The Aldehyde Dehydrogenase ALDH2*2 Allele Exhibits Dominance over ALDII2*1 in Transduced HeLa Cells, *Journal of Clinical Investigation*, 96:2180-6 (1995).

Xiao et al., The Mutation in the Mitochondrial Aldehyde Dehydrogenase (ALDH2) Gene Responsible for Alcohol-induced Flushing Increases Turnover of the Enzyme Tetramers in a Dominant Fashion, *Journal of Clinical Investigation*, 98(9):2027-32 (1996).

Yamauchi et al., Polymorphisms in Alcohol Metabolizing Enzyme Genes and Alcoholic Cirrhosis in Japanese Patients: A Multivariate Analysis, *Hepatology*, 22(4):1136-42 (1995).

Yin et al., Genetic polymorphism and activities of human lung alcohol and aldehyde dehydrogenases: Implications for ethanol metabolism and cytotoxicity, *Biochemical Genetics*, 30:3-4 (1992).

Yokoyama et al., Alcohol and Aldehyde Dehydrogenase Gene Polymorphisms and Oropharyngolaryngeal, Esophageal and Stomach Cancers in Japanese Alcoholics, Carcinogensis, 22(3):433-9 (2001).

Yoshida et al., Genetics of Human Alcohol-Metabolizing Enzymes, *Progress in Nucleic Acid Research and Molecular Biology*, 40:255-87 (1991).

Takeshita, Gene-Environmental Interactions in Alcohol-Related Health Problems—Contributions of Molecular Biology to Behavior Modifications, *Jp. J. Hygiene*, 58(2):254-9 (2003). English Abstract.

United States Patent and Trademark Office, Final Office Action for U.S. Appl. No. 13/529,695, (Jul. 9, 2014).

United States Patent and Trademark Office, Non-Final Office Action for U.S. Appl. No. 13/376,933, (Jan. 5, 2015).

United States Patent and Trademark Office, Non-Final Office Action for U.S. Appl. No. 13/529,695 (Oct. 16, 2013).

Yamauchi, Polymorphism and its gene ALDH and CYP2E1, ADH, *Jp. J. Clin. Pharmacol. Therapeut.*, 34(4):155-61 (2003). In Japanese.

4-METHYLPYRAZOLE FORMULATIONS FOR INHIBITING ETHANOL INTOLERANCE

1. RELATED APPLICATIONS

This application is a continuation of U.S. patent application Ser. No. 12/797,594, filed Jun. 9, 2010, which is a continuation-in-part of U.S. patent application Ser. No. 10/591,735, filed Jul. 23, 2007, which is a 35 U.S.C. §371 U.S. National Stage Entry of International Patent Application No. PCT/US05/07273, filed Mar. 3, 2005, which claims the benefit of U.S. Provisional Application No. 60/642,007, filed Jan. 6, 2005, and U.S. Provisional Application No. 60/550,261, filed Mar. 3, 2004, all of which applications are herein incorporated by reference in their entireties. This application also claims the benefit of U.S. Provisional Application No. 61/185,884, filed Jun. 10, 2009, which application is herein incorporated by reference in its entirety.

2. TECHNICAL FIELD

Provided herein are methods, compositions and formulations to prevent or ameliorate ethanol intolerance, reduce or ameliorate symptoms associated with acetaldehyde accumulation, for example, accompanying ethanol consumption, or reduce the risk of diseases or disorders caused by acetaldehyde accumulation, comprising administering 4-MP, or physiologically acceptable salts thereof, to subjects with reduced or absent aldehyde dehydrogenase subtype 2 (ALDH2) activity.

3. BACKGROUND OF THE INVENTION

Ethanol consumed by a person is removed from the bloodstream, in large part, in a two-step pathway in which ethanol is oxidized by alcohol dehydrogenase to acetaldehyde, that is in turn quickly metabolized into acetic acid by aldehyde dehydrogenase subtype 2 (ALDH2), a mitochondrial liver enzyme (see FIG. 1). Acetaldehyde acts as a toxin in the human body, and is linked to acute symptoms such as facial flushing, tachycardia, shortness of breath, dizziness, nausea, vomiting and headache (Inoue et al., *Alcoholism: Clinical and Experimental Research* 1984, 8, 319-322; Inoue et al., *Japan. J. Pharmacol.* 1985, 38, 43-48), as well as to increased long-term health risks for cancers of the upper digestive tract, breast cancer, liver disease, Alzheimer's disease, asthma, hypertension and myocardial infarction (Enomoto et al., *Hepatology* 1991, 13, 1071-5; Takada et al., *Alcohol.* 1994, 29, 719-27; Chao et al., *Hepatology* 1994, 19, 360-6; Yamauchi et al. *Hepatology* 1995, 22, 1136-42; Yokoyama et al., *Carcinogenesis.* 2001 22(3), 433-439; Ohsawa et al., *J. Hum. Genet.* 2003, 48, 404-409; Visapää et al., *Gut* 2004, 53, 871-876; and references cited therein).

A significant portion of the human population is "ALDH2 deficient." For example, East Asian populations carry a variant allele of ALDH2 (ALDH2*2) that encodes for an enzyme where a glutamic acid at position 487 is substituted with lysine (K487 ALDH2; Chen et al., *Am. J. Hum. Genet.* 1999, 65(3), 795-807). The K487 ALDH2 enzyme is associated with reduced or absent enzyme activity and increased enzyme turnover (Crabb et al., *J. Clin. Invest.* 1989, 83, 314-6; Xiao et al., *J. Clin. Invest.* 1996, 98, 2027-32; Wall et al., *Annals of Internal Medicine* 1997, 127(5), 376-379). The ALDH2*2 allele is dominant, such that persons who are both heterozygotes and homozygotes for the ALDH2*2 allele are deficient in ALDH2 activity (Crabb et al., *J. Clin. Invest.* 1989, 83, 314-6). People who express the ALDH2*2 allele exhibit alcohol-related sensitivity, for example, facial flushing, tachycardia, etc., as well as high blood acetaldehyde levels, when drinking small portions of ethanol (Bosron et al., *Hepatology* 1986, 6, 502-510; Goedde et al., *Hum. Genet.* 1992, 88, 344-346; Xiao et al., *J. Clin. Invest.* 1995, 96, 2180-2186). Moreover, people who express the ALDH2*2 allele also exhibit increased long-term health risks for cancers of the upper digestive tract, breast cancer, liver disease, Alzheimer's disease, hypertension and myocardial infarction (Yokoyama et al., *Carcinogenesis.* 2001 22(3), 433-439; Ohsawa et al., *J. Hum. Genet.* 2003, 48, 404-409).

Also prevalent in East Asian populations is a variant allele of alcohol dehydrogenase subtype 2 (ADH2*2) that encodes for an enzyme where an arginine at position 47 is substituted with histidine (R47H ADH2; Matsuo et al., *Carcinogenesis* 2006, 27(5), 1018-1023; Tamakoshi et al., *Alcohol* 2003, 38, 407-410). The R47H ADH2 enzyme is "superactive," exhibiting a $V_{max}$ about 40 times higher than the less active R47 ADH2 enzyme encoded by the more common allele (ADH2*1) (Bosron et al., *Hepatology* 1986, 6, 502-510; Yoshida et al., *Prog. Nucleic Acid Res. Mol. Biol.* 1991, 40, 255-287). The ADH2*2 allele is associated with the accumulation of acetaldehyde, in that people who express the ADH2*2 allele experience an increase in the steady-state concentration of blood or intrahepatic acetaldehyde in their bodies when they drink alcohol (Crabb et al., *Proc. Nutr. Soc.* 2004, 63(1), 49-63).

A recognized ADH inhibitor, 4-methylpyrazole (also known as fomepizole or 4-MP), has been approved by the U.S. Food and Drug Administration for the treatment of ethylene glycol or methanol poisoning. See, e.g., Scalley et al., *American Family Physician* 2002, 66, 807-812. As a treatment for ethylene glycol or methanol poisoning, the administration of 4-MP generally requires intravenous infusion under the supervision of a doctor in relatively large doses, e.g., 50 mg/kg or more over time (a 15 mg/kg loading dose given intravenously over 30 minutes, followed by 10 mg/kg every 12 hours for 4 doses, then 15 mg/kg every 12 hours; see Casavant, *Pediatrics* 2001, 107(1), 170). However, administration of such large doses of 4-MP itself has been reported to cause side effects similar to ALDH2 deficiency including flushing, headache and nausea. See Jacobsen et al., *Alcoholism: Clinical and Experimental Research* 1988, 12, 516-522. Further, high doses of 4-MP inhibit ADH activity to an extent that human subjects treated with 4-MP can have much higher blood ethanol concentrations than when not treated with 4-MP, leading to relatively lengthy periods of time during which the subject is under the influence of ethanol. See Jacobsen et al., *Alcoholism: Clinical and Experimental Research* 1996, 20, 804-809.

4-MP has been administered as an "alcohol metabolism enhancer" to treat the symptoms of increased aldehyde accumulation in "alcohol intolerant persons." See, e.g., Japanese Unexamined Patent Application Publication No. S57-106620. However, such administration has not been shown to be consistently helpful for all alcohol intolerant persons. As explained above, alcohol intolerance persons are members of genetic subpopulations which express different polymorphisms of the ALDH2 and ADH2 genes. These polymorphisms result in different alcohol-related sensitivities and/or to different steady-state acetaldehyde concentrations in alcohol intolerant persons when they drink alcohol. Accordingly, a dose of 4-MP found to be helpful to treat one genetic subpopulation of alcohol intolerance persons may not be equally helpful, or may even be ineffective, to treat another genetic subpopulation of alcohol intolerance persons.

What remains to be determined are solutions to address the adverse consequences of acetaldehyde accumulation in those subpopulations of alcohol intolerant persons that express specific polymorphisms of the ALDH2 and ADH2 genes. Preferably, such solutions will minimally impact the ethanol elimination rate and thereby avoid the consequence of having relatively lengthy periods of time during which the subject is under the influence of ethanol, and avoid the undesirable side-effects associated with higher doses of 4-MP.

4. SUMMARY OF THE INVENTION

In one aspect, methods are provided for preventing, reducing or ameliorating a symptom of ethanol intolerance, or acetaldehyde accumulation, in a subject with reduced or absent aldehyde dehydrogenase subtype 2 (ALDH2) activity. In certain embodiments, the subject with reduced or absent ALDH2 activity is homozygous for alcohol dehydrogenase subtype 2*1 (ADH2*1/ADH2*1) or is heterozygous for alcohol dehydrogenase subtypes 2*1 and 2*2 (ADH2*1/ADH2*2). In certain embodiments, the subject with reduced or absent ALDH2 activity is homozygous for alcohol dehydrogenase subtype 2*2 (ADH2*2/ADH2*2).

In certain aspects, methods are provided for preventing or ameliorating a symptom of ethanol intolerance in a subject with reduced or absent aldehyde dehydrogenase subtype 2 (ALDH2) activity comprising administering 4-MP, or a physiologically acceptable salt of 4-MP, to the subject. In certain embodiments, the subject with reduced or absent ALDH2 activity is homozygous for alcohol dehydrogenase subtype 2*1 (ADH2*1/ADH2*1) or is heterozygous for alcohol dehydrogenase subtypes 2*1 and 2*2 (ADH2*1/ADH2*2). In certain embodiments, the subject with reduced or absent ALDH2 activity is homozygous for alcohol dehydrogenase subtype 2*2 (ADH2*2/ADH2*2).

In certain aspects, methods are provided for preventing, reducing or ameliorating a symptom associated with acetaldehyde accumulation in a subject with reduced or absent aldehyde dehydrogenase subtype 2 (ALDH2) activity comprising administering 4-MP, or a physiologically acceptable salt of 4-MP, to the subject. In certain embodiments, the subject with reduced or absent ALDH2 activity is homozygous for alcohol dehydrogenase subtype 2*1 (ADH2*1/ADH2*1) or is heterozygous for alcohol dehydrogenase subtypes 2*1 and 2*2 (ADH2*1/ADH2*2). In certain embodiments, the subject with reduced or absent ALDH2 activity is homozygous for alcohol dehydrogenase subtype 2*2 (ADH2*2/ADH2*2). In certain embodiments, the acetaldehyde accumulation accompanies ethanol consumption.

A symptom of ethanol intolerance, or acetaldehyde accumulation, in a subject can be, for example, selected from the group consisting of flushing, elevated heart rate, palpitations, hypotension, nausea, dizziness, headache, vomiting, diarrhea, upset stomach, ataxia, and confused consciousness.

In another aspect, methods are provided for reducing a likelihood or risk in a subject with reduced or absent aldehyde dehydrogenase subtype 2 (ALDH2) for a disease or disorder caused by exposure to acetaldehyde. In certain embodiments, the acetaldehyde is a product of ethanol consumption by the subject. In certain embodiments, the subject with reduced or absent ALDH2 activity is homozygous for alcohol dehydrogenase subtype 2*1 (ADH2*1/ADH2*1) or is heterozygous for alcohol dehydrogenase subtypes 2*1 and 2*2 (ADH2*1/ADH2*2). In certain embodiments, the subject with reduced or absent ALDH2 activity is homozygous for alcohol dehydrogenase subtype 2*2 (ADH2*2/ADH2*2).

Conditions or diseases associated with exposure to acetaldehyde caused by, for example, the subject's consumption of ethanol, include, for example and without limitation, hangover, alcoholic gastritis, alcohol-induced liver damage, upper aerodigestive tract cancers, digestive tract cancers, breast cancer, late-onset Alzheimer's disease, hypertension, myocardial infarction, Parkinson's disease, amyotropic lateral sclerosis, and cerebral ischemia. In certain embodiments, diseases associated with the consumption of ethanol include upper aerodigestive tract cancers, digestive tract cancers, breast cancer, late-onset Alzheimer's disease, hypertension, myocardial infarction, Parkinson's disease, amyotropic lateral sclerosis, and cerebral ischemia.

In yet other aspects, methods are provided for reducing a likelihood or risk in a subject for a disease or disorder caused by exposure to acetaldehyde comprising administering to a subject in need thereof an amount of a 4-MP, or a physiologically acceptable salt of 4-MP, effective to increase catabolism of acetaldehyde in the subject, thereby reducing the likelihood or risk for the disease or disorder. In certain embodiments, the acetaldehyde is a product of ethanol consumption.

In certain embodiments, the methods provided herein comprise administering to the subject about 0.1 mg to about 5 mg 4-MP, or the equivalent mass of 4-MP in a physiologically acceptable salt form, per kilogram of the subject's body mass. In certain embodiments, the methods provided herein comprise administering to the subject about 0.1 mg to about 4 mg 4-MP, or the equivalent mass of 4-MP in a physiologically acceptable salt form, per kilogram of the subject's body mass. In certain embodiments, the methods provided herein comprise administering to the subject about 0.1 mg to about 1.0 mg 4-MP, or the equivalent mass of 4-MP in a physiologically acceptable salt form, per kilogram of the subject's body mass. In certain embodiments, the methods provided herein comprise administering to the subject about 0.5 mg to about 1.0 mg 4-MP, or the equivalent mass of 4-MP in a physiologically acceptable salt form, per kilogram of the subject's body mass.

In certain embodiments, the methods provided herein comprise administering to the subject about 0.1 mg to about 10 mg 4-MP, or the equivalent mass of 4-MP in a physiologically acceptable salt form, per kilogram of the subject's body mass. In certain embodiments, the methods provided herein comprise administering to the subject about 1.0 mg to about 10 mg 4-MP, or the equivalent mass of 4-MP in a physiologically acceptable salt form, per kilogram of the subject's body mass. In certain embodiments, the methods provided herein comprise administering to the subject about 5 mg to about 10 mg 4-MP, or the equivalent mass of 4-MP in a physiologically acceptable salt form, per kilogram of the subject's body mass.

In certain embodiments, the methods provided herein comprise administering to the subject about 0.1 mg to about 10 mg, about 0.05 mg/kg to about 5 mg/kg, about 0.1 mg to about 5 mg, about 0.1 mg to about 4.5 mg, about 0.1 mg to about 4 mg, about 0.1 mg to about 3.5 mg, about 0.1 mg to about 3 mg, about 0.1 mg to about 2.5 mg, about 0.1 mg to about 2 mg, about 0.1 mg to about 1.5 mg, about 0.1 mg to about 1.0 mg, about 0.1 mg to about 0.9 mg, about 0.1 mg to about 0.7 mg, about 0.1 mg to about 0.5 mg, about 0.2 mg to about 0.9 mg, about 0.3 mg to about 0.7 mg, about 0.5 mg to about 2 mg, about 0.5 mg to about 0.9 mg, about 0.5 mg to about 1.0 mg, about 1.0 mg to about 10 mg, about 1.0 mg to about 5 mg, about 1.0 mg to about 4.5 mg, about 1.0 mg to about 4 mg, about 1.0 mg to about 3.5 mg, about 1.0 mg to about 3 mg, about 1.0 mg to about 2.5 mg, about 1.0 mg to about 2 mg, about 1.0 mg to about 1.5 mg, about 2 mg to about 4 mg of 4-MP, or about 5 mg to about 10 mg, or the equivalent mass of 4-MP in a physiologically acceptable salt form, per kilogram of the subject's body mass.

In certain embodiments, the methods provided herein comprise administering to the subject about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.5 mg, about 2 mg, about 2.5 mg, about 3 mg, about 3.5 mg, about 4 mg, about 4.5 mg, about 5 mg, about 6 mg, about 7 mg, about 8 mg, about 9 mg, or about 10 mg 4-MP, or the equivalent mass of 4-MP in a physiologically acceptable salt form, per kilogram of the subject's body mass.

In certain embodiments, 4-MP is orally administered.

In certain embodiments, 4-MP is orally administered before the subject consumes ethanol.

In certain embodiments, 4-MP is orally administered about two hours to about fifteen minutes before the subject consumes ethanol.

In other embodiments, 4-MP is orally administered concurrently with the subject's consumption of ethanol or after the subject has consumed ethanol.

In certain embodiments, the percent reduction in the subject's ethanol elimination rate is no more than about 10% in comparison to the ethanol elimination rate of a subject not administered 4-MP.

In certain embodiments, the methods comprise administering an effective amount of 4-MP that reduces acetaldehyde accumulation by about 25% to about 60% as compared to a subject not administered 4-MP. In certain embodiments, the methods comprise administering an effective amount of 4-MP that reduces acetaldehyde accumulation by about 50% to about 60% as compared to a subject not administered 4-MP.

In certain embodiments, the methods comprise administering an amount of 4-MP or a physiological acceptable salt of 4-MP effective to reduce or inhibit ethanol-oxidizing activity of alcohol dehydrogenase in the subject.

In certain embodiments, an effective amount of a hydrochloride salt of 4-MP is administered.

In certain embodiments, the ALDH2 and ADH2 genotypes of the subject are determined prior to administration of 4-MP.

In other aspects, the present application provides a composition or formulation comprising 4-MP, or a physiologically acceptable salt thereof, and a physiologically acceptable excipient, optionally provided as a unit dosage, suitable for oral administration to a subject.

5. DESCRIPTION OF FIGURES

FIG. 1. Metabolism of ethanol.

Figure 2:
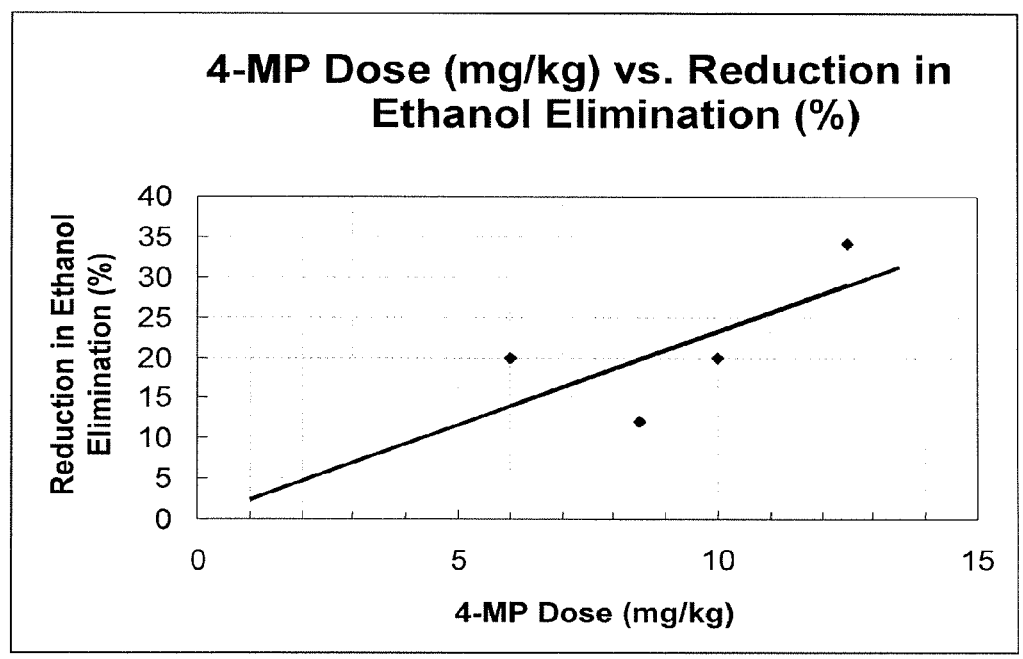

FIG. 2. Graph of milligrams 4-MP per kilogram body mass administered to human subjects versus percent reduction in ethanol elimination rate. Linear least squares regression was used to fit a line to data obtained from the sources cited in Section 8.

Figure 3:
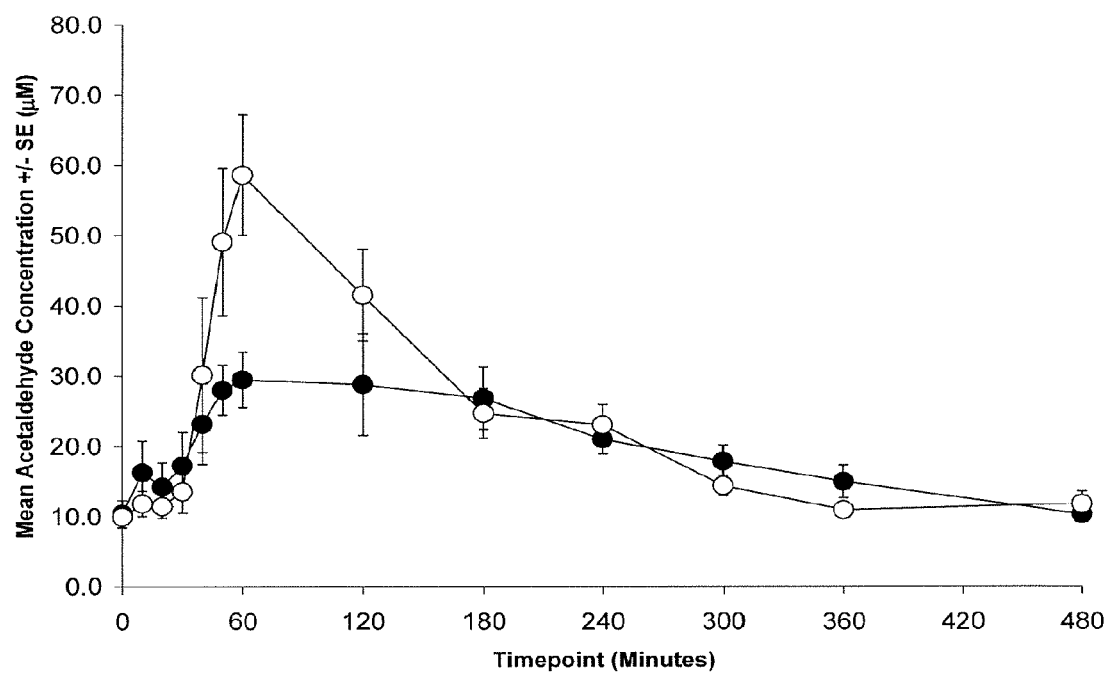

FIG. 3. Graph of mean serum acetaldehyde concentration measured in subjects with reduced ALDH2 activity, who are also ADH2*1/ADH2*1 homozygous or ADH2*1/ADH2*2 heterozygous, following dosage with 1 mg/kg 4-MP (filled circles); comparison with placebo (open circles).

Figure 4:
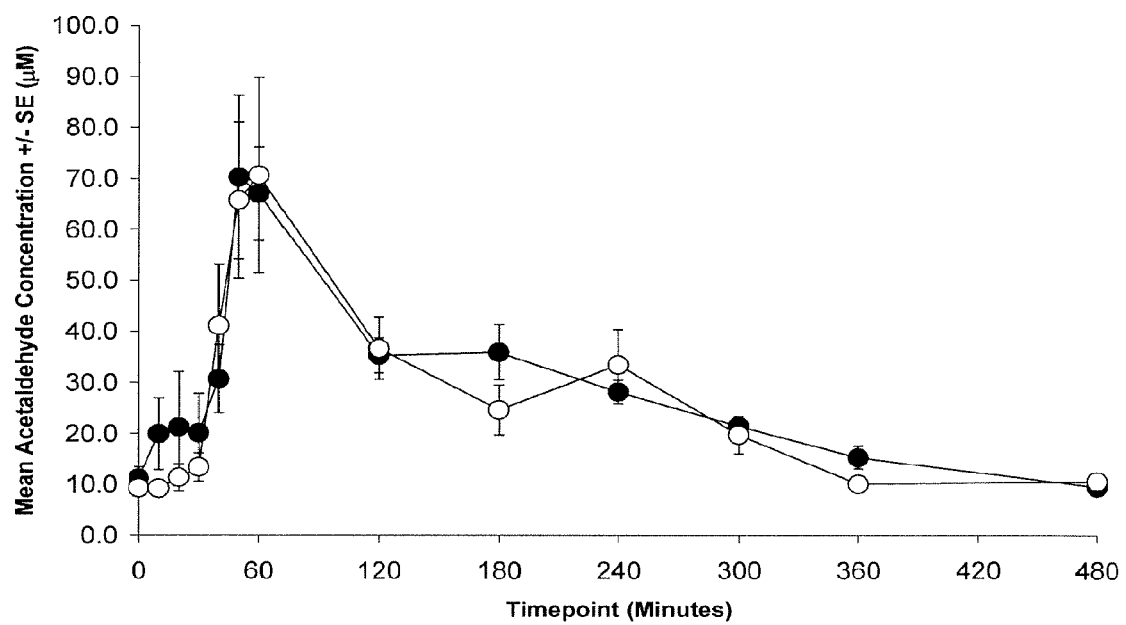

FIG. 4. Graph of mean serum acetaldehyde concentration measured in subjects with reduced or absent ALDH2 activity, who are also ADH2*2/ADH2*2 homozygous, following dosage with 1 mg/kg 4-MP (filled circles); comparison with placebo (open circles).

Figure 5:
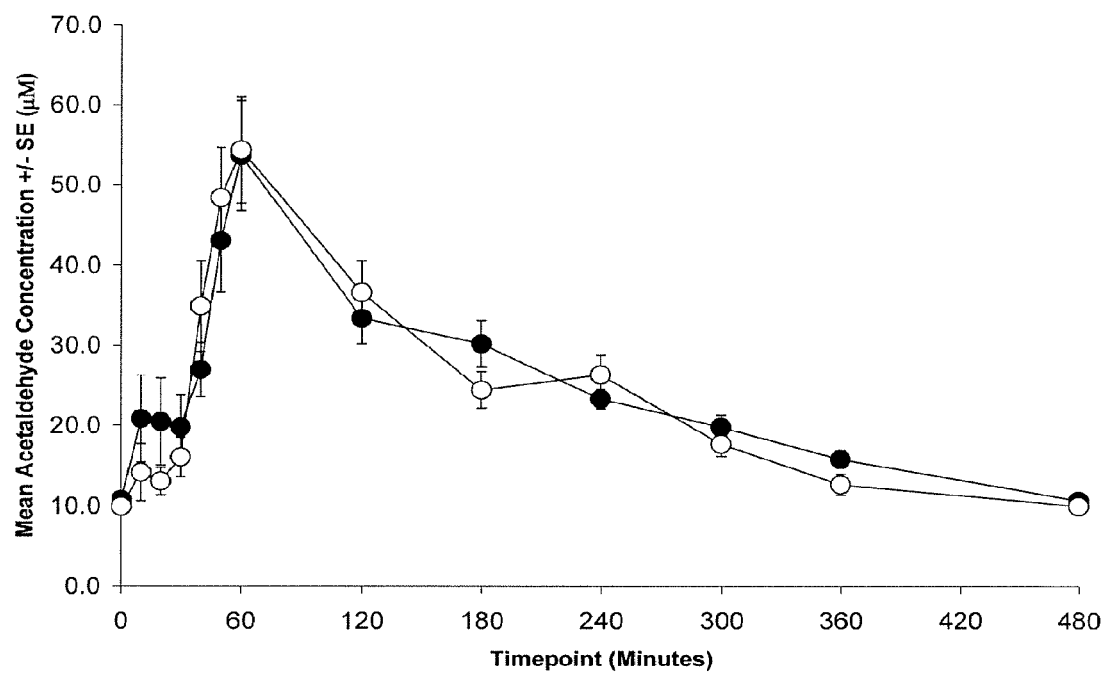

FIG. 5. Graph of mean serum acetaldehyde concentration across all subjects with reduced or absent ALDH2 activity, following dosage with 4-MP (filled circles); comparison with placebo (open circles).

6. TERMINOLOGY

Generally, the nomenclature used herein and the laboratory procedures in medicinal chemistry, biochemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

As used herein, "about" indicates a range of +/−10%. For example, "about 10 mg 4-MP" means a range of from 9.0 mg to 11.0 mg 4-MP.

The term "subject" refers to animals such as mammals, including, but not limited to, primates (e.g., humans), monkeys, cattle, sheep, goats, horses, dogs, cats, rabbits, pigs, deer, bear, rats, mice and the like. In preferred embodiments, the subject is a human.

The terms "treat," "treating" or "treatment," as used herein, refers to a method of alleviating or abrogating a disorder and/or its attendant symptoms.

The terms "prevent," "preventing" or "prevention," in certain embodiments, refer to a method of barring a subject from acquiring a disorder and/or its attendant symptoms. In certain embodiments, the terms "prevent," "preventing," or "prevention," refer to a method of reducing the likelihood or risk of a subject acquiring a disorder and/or its attendant symptoms.

The term "physiologically acceptable salt" or "acceptable salt form," as used herein, refers to the relatively nontoxic, inorganic and organic acid addition salts of the compounds provided herein.

The term "symptom" as used herein is interchangeable with "sign." Therefore, as used herein "symptom" refers to a physical condition which indicates a particular illness or disorder (e.g., *Longman Dictionary of Contemporary English* 1995. Third Edition) detectable by the subject suffering from a particular disease or disorder or detectable by a person other than the subject without verbal information from said subject.

The phrase "symptom of acetaldehyde accumulation accompanying ethanol consumption," as used herein refers to any symptom experienced by subjects with reduced or absent aldehyde dehydrogenase subtype 2 (ALDH2) activity when consuming ethanol. Symptoms can include, but are not limited to, flushing, elevated heart rate, palpitations, hypotension, nausea, dizziness, headache, vomiting, diarrhea, upset stomach, ataxia, or confused consciousness. See, for example, Ward et al., *Alcohol and Alcoholism* 1994, 29, 433-438.

The phrase "subject with reduced or absent aldehyde dehydrogenase subtype 2 (ALDH2) activity" refers to a subject that is a homozygous or heterozygous carrier of the variant ALDH2*2 allele of the ALDH2 gene as described in Crabb et al., *J. Clin. Invest.* 1989, 83, 314-6, Goedde et al., *Hum. Genet.* 1992, 88, 344-346, and Xiao et al., *J. Clin. Invest.* 1995, 96, 2180-2186, which are incorporated herein by reference in their entireties, or to a subject that expresses any variant ALDH2 enzyme that exhibits less activity than the normal ALDH2 enzyme as determined by the aldehyde dehydrogenase activity assay described in Xiao et al., *J. Clin. Invest.* 1995, 96, 2180-2186.

The phrase "the subject is homozygous for alcohol dehydrogenase subtype 2*1 (ADH2*1/ADH2*1) or heterozygous for alcohol dehydrogenase subtypes 2*1 and 2*2 (ADH2*1/ADH2*2)" refers to a subject that is a homozygous or heterozygous carrier of the more common ADH2*1 allele, as described in Crabb et al., *J. Clin. Invest.* 1989, 83, 314-6, and Matsuo et al., *Carcinogenesis* 2006, 27(5), 1018-1023, which are incorporated herein by reference in their entireties.

The phrase "the subject is homozygous for alcohol dehydrogenase subtype 2*2 (ADH2*2/ADH2*2)" refers to a subject that is a homozygous carrier of the variant ADH2*2 allele, as described in Crabb et al., *J. Clin. Invest.* 1989, 83, 314-6, and Matsuo et al., *Carcinogenesis* 2006, 27(5), 1018-1023, which are incorporated herein by reference in their entireties.

As used herein, "ethanol intolerance," refers to a condition in which a subject experiences a symptom of acetaldehyde accumulation accompanying ethanol consumption. Symptoms of ethanol intolerance, or acetaldehyde accumulation, may include, but are not limited to, flushing, elevated heart rate, palpitations, hypotension, nausea, dizziness, headache, vomiting, diarrhea, upset stomach, ataxia, or confused consciousness. See, for example, Ward et al., *Alcohol and Alcoholism* 1994, 29, 433-438.

As used herein, "ethanol elimination rate" refers to the reduction in ethanol concentration in a subject's bloodstream over time after the subject has ingested ethanol. Typically, an ethanol elimination rate can be expressed in terms of millimole ethanol/kilogram subject body mass/hour. Techniques for blood sampling and analysis of ethanol levels in blood are well known to those of skill in the art. See, e.g., Inoue et al., *Alcoholism: Clinical and Experimental Research* 1984, 8, 319-322, incorporated herein by reference in its entirety. A "percent change in ethanol elimination rate," can be calculated as follows:

Percent Change in EtOH Elimination=

$$\left(1 - \frac{\text{Subject's EtOH Elimination Rate After Taking 4-}MP}{\text{Subject's EtOH Elimination Rate Prior to Taking }MP\text{-}4}\right) \times 100$$

where EtOH represents ethanol, and a number for a percent change in ethanol elimination that is less than 100 is a reduction in the percent change in EtOH elimination. Blood ethanol levels can also be calculated, for example, based on algorithms utilizing the amount of ethanol consumed by a subject, the subject's body mass, and time period since the consumption of ethanol, or, as another example, blood ethanol levels can be extrapolated from analysis of a subject's breath, and the like, as known to those of skill in the art.

As used herein, "acetaldehyde accumulation" refers to the production of acetaldehyde in a subject that has consumed ethanol. Techniques for blood sampling and analysis of acetaldehyde levels in blood are well known to those of skill in the art. See, e.g., Inoue et al., *Alcoholism: Clinical and Experimental Research* 1984, 8, 319-322. Also see, e.g., Stowell, *Clin. Chim. Acta.* 1979, 98, 201-5, McCarver-May et al., *Journal of Analytical Toxicology* 1997, 21, 134-141, and Nagy et al., *Rapid Communications in Mass Spectrometry* 2004, 18, 2473-2478, which are incorporated herein by reference in their entireties. Maximal concentrations of acetaldehyde accumulation typically follow fifteen minutes to one hour following ethanol consumption in a subject with reduced or absent ALDH2 activity. Where a "percent change in acetaldehyde accumulation" is used herein, this will be understood to mean the change in the maximal concentrations of acetaldehyde in a subject with reduced or absent ALDH2 activity, that can be calculated as follows:

Percent Change in Acetaldehyde Accumulation=

$$\left(1 - \frac{\text{Max. Acetaldehyde } Conc. \text{ After Taking 4-}MP}{\text{Max. Acetaldehyde } Conc. \text{ Prior to Taking }MP\text{-}4}\right) \times 100$$

where a number for a percent change in acetaldehyde accumulation that is less than 100 is a reduction in the percent change in acetaldehyde accumulation. Blood acetaldehyde concentrations can also be extrapolated from analysis of a subject's breath, or from measurable physiological changes in other parameters, such as heart rate or flushing, and the like, as known to those of skill in the art.

As defined herein, where the mass of 4-MP is specified, for example, "10 mg 4-MP," that amount refers to the equivalent mass of 4-MP in its free base form. Thus, for example, if 10 mg 4-MP in a given salt form is to be administered in a formulation disclosed herein, one of skill in the art can make the necessary conversion using the molecular masses of the salt form of 4-MP and of the free base form of 4-MP to determine the actual mass of that salt form of 4-MP necessary to obtain the equivalent mass of 10 mg 4-MP in its free base form. As another example, if 10 mg 4-MP in a free base form is to be administered in a formulation disclosed herein, then no conversion is necessary.

As used herein, a "stable formulation" refers to a formulation which displays physical stability and/or chemical stability under storage conditions. Unless otherwise indicated, storage conditions are intended to cover those conditions in which pharmaceutical formulations are typically stored, and may include, for example, temperatures of up to about 25° C.; up to about 26° C.; up to about 27° C.; up to about 28° C.; up to about 29° C.; up to about 30° C.; up to about 31° C.; up to about 32° C.; up to about 33° C.; up to about 34° C.; up to about 35° C.; up to about 36° C.; up to about 37° C.; up to about 39° C.; or up to about 40° C.; relative humidities of up to about 10%; up to about 15%; up to about 20%; up to about 25%; up to about 30%; up to about 35%; up to about 40%; up to about 45%; up to about 50%; up to about 55%; up to about 60%; up to about 65%; up to about 70%; up to about 75%; up to about 80%; up to about 85%; up to about 90%; up to about 95%; or up to about 100%; and other conditions as specified.

As used herein, "chemical stability" of a formulation refers to the chemical stability of the active pharmaceutical unit (i.e., 4-MP) in a unit dosage form of the formulation, for example, a tablet or capsule of the formulation. Typically, chemical stability is evaluated through assaying the content of the active pharmaceutical unit in the formulation. Typically, a chemically stable formulation is one which displays limited degradation or loss of potency of the active pharmaceutical ingredient, or which displays limited loss of content of the active pharmaceutical ingredient, upon storage. Typical formulations provided herein will retain at least about 99%, at least about 98%, at least about 97%, at least about 96%, at least about 95%, at least about 94%, at least about 93%, at least about 92%, at least about 91%, or at least about 90% content of their active pharmaceutical ingredient upon storage for 8 months or more at room temperature and at relative humidities of up to about 60%±5%.

As used herein, "physical stability" of a formulation refers to the physical integrity of a unit dosage form of the formulation, for example, a tablet or capsule of the formulation.

Typically, physical stability is evaluated through a visual inspection of the physical appearance of the unit dosage form. The physical appearance of the unit dosage form may include such physical characteristics as form, color, shape, odor, surface texture, and presence or absence of physical flaws, including the presence or absence of breaks or tears in the unit dosage form. Where the unit dosage form is a capsule, a physically stable formulation is typically one in which the capsule displays no deformity, breakage, or leakage of capsule contents. Typical formulations provided herein will be physically stable upon storage for 8 months or more at room temperature and at relative humidities of up to about 60%±5%.

The term "room temperature," as used herein, refers to 25° C.±2° C.

As used herein, the term "dose" or "dosage" refers the amount of 4-MP that an individual takes or is administered at one time. The term "unit dosage form" refers to a physically discrete unit, such as a capsule, tablet or volume of liquid, suitable as a unitary dosage for a human subject. Each unit contains a predetermined quantity of 4-MP that was discovered as a result of methods provided herein to produce the desired pharmacokinetic profile which yields the desired therapeutic effect. The dosage unit is composed of 4-MP in association with at least one pharmaceutically acceptable carrier, salt, excipient, or combination thereof. By way of example, an 170 mg 4-MP dose refers to amount of 4-MP a person can take at one time, where the dose can be divided into two 85 mg dosage units, for example, two 85 mg 4-MP tablets.

The term "effective amount" as used herein refers to the amount of 4-MP, or physiologically acceptable salt thereof, that is sufficient to produce a desirable or beneficial effect when contacted, for example, to an alcohol dehydrogenase enzyme, or, as another example, when administered to a subject. In certain embodiments, the "effective amount" is, for example, the amount to prevent, reduce or ameliorate a symptom associated with acetaldehyde accumulation in a subject accompanying ethanol consumption, or to reduce the likelihood or risk in a subject for a disease or disorder caused by consumption of ethanol.

The term "AUC" as used herein, refers to the area under the curve of a plot of serum acetaldehyde concentration versus time following administration of 4-MP to a subject. In certain embodiments, the AUC is bounded by 0 to 8 hours ($AUC_{0-8H}$).

The term "AUC mean" as used herein, refers to the area under the curve of a plot of mean serum acetaldehyde concentration versus time following administration of 4-MP to subjects of a sample population. In certain embodiments, the AUC mean is bounded by 0 to 8 hours ($AUC_{0-8H}$ mean).

The term "$C_{max}$" as used herein, refers to the maximum serum acetaldehyde concentration following administration of 4-MP to a subject.

The term "$C_{max}$ mean" as used herein, refers to the mean maximum serum acetaldehyde concentration following administration of 4-MP to subjects of a sample population.

The term "P-value" as used herein, refers to the probability of obtaining a certain result. The lower the P-value, the less likely, and therefore, the more statistically significant the result. In certain embodiments, a P-value of 0.05 corresponds to a 5% chance of obtaining a certain result.

The term "SE" as used herein, refers to the standard error of the mean of a sample population. In certain embodiments, SE may refer to an estimate of the standard deviation calculated from sample data measured in a sample population.

7. DETAILED DESCRIPTION OF THE INVENTION

Provided herein are methods, compositions and formulations useful for reducing or ameliorating the severity of, or preventing, an adverse physiological symptom associated with acetaldehyde accumulation accompanying ethanol consumption in a subject with reduced or absent aldehyde dehydrogenase subtype 2 activity. The subject may express specific polymorphisms of the aldehyde dehydrogenase subtype 2 (ALDH2) gene and the alcohol dehydrogenase subtype 2 (ADH2) gene. For example, the subject may be a carrier of the variant ALDH2*2 allele of the ALDH2 gene, and may further be a carrier of the variant ADH2*2 allele of the ADH2 gene, as described herein.

As explained below, the methods provided comprise the administration of 4-MP or a physiologically acceptable salt of 4-MP. Without intending to be bound by any particular theory or mechanism, it is believed that 4-MP acts to inhibit alcohol dehydrogenase (ADH) to reduce the accumulation of acetaldehyde production that results from the consumption of ethanol.

7.1. Methods to Prevent or Ameliorate a Symptom of Ethanol Intolerance or of Acetaldehyde Accumulation in a Subject with Reduced or Absent ALDH2 Activity In one aspect, provided herein are methods for preventing, reducing or ameliorating a symptom of ethanol intolerance, or acetaldehyde accumulation, in a subject with reduced or absent aldehyde dehydrogenase subtype 2 (ALDH2) activity. In certain embodiments, the subject with reduced or absent ALDH2 activity is homozygous for alcohol dehydrogenase subtype 2*1 (ADH2*1/ADH2*1) or is heterozygous for alcohol dehydrogenase subtypes 2*1 and 2*2 (ADH2*1/ADH2*2). In certain embodiments, the subject with reduced or absent ALDH2 activity is homozygous for alcohol dehydrogenase subtype 2*2 (ADH2*2/ADH2*2).

In certain embodiments, the methods comprise administering 4-methylpyrazole (4-MP) to the subject.

4-Methylpyrazole (4-MP, also known as fomepizole) is commercially available from chemical suppliers, including, for example, Sigma Aldrich (St. Louis, Mo.), and can also be synthesized easily in commercially viable quantities of pharmaceutical grade.

In certain embodiments, the methods further comprise determining the ALDH2 and ADH2 genotype of the subject using methods known in the art, as described, for example, in Enomoto et al., *J. Gastroenterol.* 1991, 26, 440-447 (genotyping of ALDH2 gene), in Nishiyori et al., *Clinical Chem.* 2000, 48, 563-564 (genotyping of ADH2 gene), and in Tamakoshi et al., *Alcohol & Alcoholism* 2003, 38(5), 407-410 (genotyping of ALDH2 and ADH2 genes) or using methods such as those described in Section 8.2.

In certain embodiments, ALDH2 and ADH2 genotypes of the subject are determined prior to administration of 4-MP. In certain embodiments, the ALDH2 genotype of the subject is determined prior to administration of 4-MP. In certain embodiments, the ADH2 genotype of the subject is determined prior to administration of 4-MP.

In certain embodiments, the methods comprise administering about 1.0 mg to about 5 mg 4-MP per kilogram of a subject's body mass, to the subject. In certain embodiments, the methods comprise administering about 1.0 mg to about 4 mg 4-MP per kilogram of a subject's body mass, to the subject. In certain embodiments, the methods comprise administering about 0.1 mg to about 1.0 mg 4-MP per kilogram of a subject's body mass, to the subject. In certain embodiments, the methods comprise administering about 0.5 mg to about 1.0 mg 4-MP per kilogram of a subject's body mass, to the subject.

In certain embodiments, the methods comprise administering about 0.1 mg to about 10 mg 4-MP per kilogram of a subject's body mass, to the subject. In certain embodiments, the methods comprise administering about 1.0 mg to about 10 mg 4-MP per kilogram of a subject's body mass, to the subject. In certain embodiments, the methods comprise administering about 5 mg to about 10 mg 4-MP per kilogram of a subject's body mass, to the subject.

In certain embodiments, the compound for use in the methods is the free base of 4-MP. In other embodiments, a physiologically acceptable salt of 4-MP can be used in the methods. In certain embodiments, a 4-MP hydrochloride salt can be used in the methods described herein.

4-MP can be administered alone or in combination with other substances or active agents. In certain embodiments, a composition comprising 4-MP and other ingredients, as described below, is administered.

4-MP can be administered according to any technique known to those of skill in the art. In certain embodiments, 4-MP can be delivered transdermally. In preferable embodiments, the subject can self-administer 4-MP to himself or herself. In preferable embodiments, 4-MP can be administered orally. When orally administered, 4-MP can be in a solid form, for example, as in a powder, tablet, capsule and the like, or in a liquid form.

In certain embodiments, the amount of 4-MP administered can be between about 0.1 mg/kg to about 5 mg/kg. In certain embodiments, the amount of 4-MP administered can be between about 0.1 mg/kg to about 4 mg/kg. In certain embodiments, the amount of 4-MP administered can be between about 0.1 mg/kg to about 1.0 mg/kg. In certain embodiments, the amount of 4-MP administered can be between about 0.5 mg/kg to about 1.0 mg/kg. In certain embodiments, the amount of 4-MP administered can be between about 1.0 mg/kg to about 5 mg/kg. In certain embodiments, the amount of 4-MP administered can be between about 1.0 mg/kg to about 4 mg/kg.

In certain embodiments, the amount of 4-MP administered can be between about 0.1 mg/kg to about 10 mg/kg. In certain embodiments, the amount of 4-MP administered can be between about 1.0 mg/kg to about 10 mg/kg. In certain embodiments, the amount of 4-MP administered can be between about 5 mg/kg to about 10 mg/kg.

As will be understood by those of skill in the art, the amounts of 4-MP to be administered, as described herein, are based on the body mass of the subject, expressed in kilograms.

In certain embodiments, the amount of 4-MP administered to the subject with reduced or absent aldehyde ALDH2 activity can be in the range between about 0.05 mg/kg to about 5 mg/kg, about 0.1 mg/kg to about 5 mg/kg, about 0.1 mg/kg to about 4.5 mg/kg, about 0.1 mg/kg to about 4 mg/kg, about 0.1 mg/kg to about 3.5 mg/kg, about 0.1 mg/kg to about 3 mg/kg, about 0.1 mg/kg to about 2.5 mg/kg, about 0.1 mg/kg to about 2 mg/kg, about 0.1 mg/kg to about 1.5 mg/kg, about 0.1 mg/kg to about 1.0 mg/kg, about 0.1 mg/kg to about 0.9 mg/kg, about 0.1 mg/kg to about 0.7 mg/kg, about 0.1 mg/kg to about 0.5 mg/kg, about 0.3 mg/kg to about 0.7 mg/kg, about 0.2 mg/kg to about 0.9 mg/kg, about 0.5 mg/kg to about 0.9 mg/kg, about 0.5 mg/kg to about 1.0 mg/kg, about 1.0 mg/kg to about 5 mg/kg, about 1.0 mg/kg to about 4.5 mg/kg, about 1.0 mg/kg to about 4 mg/kg, about 1.0 mg/kg to about 3.5 mg/kg, about 1.0 mg/kg to about 3 mg/kg, about 1.0 mg/kg to about 2.5 mg/kg, about 1.0 mg/kg to about 2 mg/kg, about 1.0 mg/kg to about 1.5 mg/kg, about 0.5 mg/kg to about 2 mg/kg, or about 2 mg/kg to about 4 mg/kg of 4-MP.

In certain embodiments, the amount of 4-MP administered to the subject with reduced or absent aldehyde ALDH2 activity can be in the range between about 0.1 mg/kg to about 10 mg/kg, about 1.0 mg/kg to about 10 mg/kg, or about 5 mg/kg to about 10 mg/kg.

In certain embodiments, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.5 mg/kg, about 2 mg/kg, about 2.5 mg/kg, about 3 mg/kg, about 3.5 mg/kg, about 4 mg/kg, about 4.5 mg/kg, or about 5 mg/kg 4-MP are administered to the subject with reduced or absent aldehyde ALDH2 activity.

In certain embodiments, about 5 mg/kg, about 6 mg/kg, about 7 mg/kg, about 8 mg/kg, about 9 mg/kg, or about 10 mg/kg 4-MP are administered to the subject with reduced or absent aldehyde ALDH2 activity.

In certain embodiments, the amount of 4-MP, or physiologically acceptable salt thereof, administered can be effective to reduce or inhibit the ethanol-oxidizing activity of alcohol dehydrogenase in the subject. In certain embodiments, the amount of 4-MP, or physiologically acceptable salt thereof, administered can be effective to reduce or inhibit the ethanol-oxidizing activity of the ADH2 enzyme in the subject.

In certain embodiments, the methods comprise determining the ADH2 genotype in a subject with reduced or absent ALDH2 activity, such that the amount of 4-MP administered to the subject is appropriate for the subject's ADH2 genotype. In certain embodiments, the amount of 4-MP administered to the subject is appropriate for the ADH2 genotype determined for the subject, so as to be optimally effective in reducing or inhibiting the ethanol-oxidizing activity of the ADH2 enzyme in the subject.

In certain embodiments, the subject with reduced or absent ALDH2 activity who is homozygous for alcohol dehydrogenase subtype 2*1 (ADH2*1/ADH2*1) or is heterozygous for alcohol dehydrogenase subtypes 2*1 and 2*2 (ADH2*1/ADH2*2) is administered about 0.1 mg/kg to about 5 mg/kg 4-MP.

In certain embodiments, the subject with reduced or absent ALDH2 activity who is homozygous for alcohol dehydrogenase subtype 2*1 (ADH2*1/ADH2*1) or is heterozygous for alcohol dehydrogenase subtypes 2*1 and 2*2 (ADH2*1/ADH2*2) is administered about 0.1 mg/kg to about 1.0 mg/kg 4-MP.

In certain embodiments, the subject with reduced or absent ALDH2 activity who is homozygous for alcohol dehydrogenase subtype 2*2 (ADH2*2/ADH2*2) is administered about 5 mg/kg to about 10 mg/kg 4-MP.

In certain embodiments, 4-MP can be administered before the subject has consumed ethanol. In certain embodiments, 4-MP can be administered about one minute, about fifteen minutes, or about one hour before the subject consumes ethanol. In certain embodiments, 4-MP can be orally administered about two hours to about fifteen minutes before the subject consumes ethanol.

In certain embodiments, 4-MP can be administered concurrent with the consumption of ethanol. In certain embodiments, 4-MP can be administered immediately before or after the consumption of ethanol. In certain embodiments, 4-MP can be administered to a subject after the subject has consumed ethanol.

It can be particularly advantageous to minimize the peak concentrations of acetaldehyde in the blood of subjects with reduced or absent ALDH2 activity, without a concomitant reduction in the rate of ethanol elimination, so as to avoid the consequence of having relatively lengthy periods of time during which the subject is under the influence of ethanol. With certain doses of 4-MP contemplated herein, that is, between about 0.1 mg/kg to about 4 mg/kg, the percent reduction in ethanol elimination rate can be negligibly or minimally impacted as discussed below.

In certain embodiments, methods are provided comprising the administration of 4-MP wherein a percent reduction in ethanol elimination ranges from about 0%, about 1%, about 2%, about 3%, about 4%, about 5% or about 6% to no more than about 10%. For example, if a subject not treated with 4-MP that has an ethanol elimination rate of 2.50 mmol/kg/hr, and has an ethanol elimination rate of 2.30 mmol/kg/hr when administered with 4-MP, than the percent reduction in ethanol elimination is 8%.

In certain embodiments, methods are provided that can have a percent reduction in the subject's ethanol elimination rate ranging from no reduction or 1-2% reduction in the ethanol elimination rate to less than about 7%, about 8%, about 9%, or about 10% reduction in the subject's rate of ethanol elimination. In certain embodiments, the methods provided result in a reduction of ethanol elimination between about 5% to about 10%. In certain embodiments, the percent reduction in the subject's ethanol elimination rate is no more than about 10% in comparison to the ethanol elimination rate of the subject not treated with 4-MP.

With the doses of 4-MP contemplated in the instant methods, the percent reduction in peak blood acetaldehyde concentrations can be reduced in a subject with reduced ALDH2 activity.

In certain embodiments, the methods provided can reduce acetaldehyde accumulation by about 50% to about 60% in a subject with reduced or absent ALDH2 activity as compared to when 4-MP is not administered to the subject. In certain embodiments, the peak acetaldehyde accumulation can be effectively eliminated or reduced by about 95%, 90%, 85%, 80%, 75%, 70%, 65%, 60%, 55%, 50%, 45%, 40%, 35%, 30%, 25%, 20%, 15%, 10% or about 5%.

In certain embodiments, the methods provided prevent or ameliorate a symptom of ethanol intolerance, or acetaldehyde accumulation, in a subject selected from the group consisting of flushing, elevated heart rate, palpitations, hypotension, nausea, dizziness, headache, vomiting, diarrhea, upset stomach, ataxia, and confused consciousness.

7.2. Methods to Reduce Likelihood or Risk for a Disease or Disorder Caused by Exposure to Acetaldehyde in a Subject with Reduced or Absent ALDH2 Activity In another aspect, provided herein are methods for reducing a likelihood or risk in a subject for a disease or disorder caused by exposure to acetaldehyde. In certain embodiments, the exposure to acetaldehyde is caused by the subject's consumption of ethanol.

In certain embodiments, the subject has reduced or absent aldehyde dehydrogenase subtype 2 (ALDH2) activity. In certain embodiments, the subject with reduced or absent ALDH2 activity is homozygous for alcohol dehydrogenase subtype 2*1 (ADH2*1/ADH2*1) or is heterozygous for alcohol dehydrogenase subtypes 2*1 and 2*2 (ADH2*1/ADH2*2). In certain embodiments, the subject with reduced or absent ALDH2 activity is homozygous for alcohol dehydrogenase subtype 2*2 (ADH2*2/ADH2*2).

In certain embodiments, the ALDH2 and ADH2 genotypes of the subject are determined prior to administration of 4-MP.

In certain embodiments, the ALDH2 genotype of the subject is determined prior to administration of 4-MP. In certain embodiments, the ADH2 genotype of the subject is determined prior to administration of 4-MP.

In certain embodiments, the compound for use in the methods is the free base of 4-MP. In other embodiments, a physiologically acceptable salt of 4-MP can be used in the methods. In certain embodiments, a 4-MP hydrochloride salt can be used in the methods described herein.

In certain embodiments, the methods comprise administering about 1.0 mg to about 5 mg 4-MP per kilogram of a subject's body mass, to the subject. In certain embodiments, the methods comprise administering about 1.0 mg to about 4 mg 4-MP per kilogram of a subject's body mass, to the subject. In certain embodiments, the methods comprise administering about 0.1 mg to about 1.0 mg 4-MP per kilogram of a subject's body mass, to the subject. In certain embodiments, the methods comprise administering about 0.5 mg to about 1.0 mg 4-MP per kilogram of a subject's body mass, to the subject.

In certain embodiments, the methods comprise administering about 0.1 mg to about 10 mg 4-MP per kilogram of a subject's body mass, to the subject. In certain embodiments, the methods comprise administering about 1.0 mg to about 10 mg 4-MP per kilogram of a subject's body mass, to the subject. In certain embodiments, the methods comprise administering about 5 mg to about 10 mg 4-MP per kilogram of a subject's body mass, to the subject.

In certain embodiments, the methods are effective to increase catabolism of acetaldehyde in the subject, thereby reducing a likelihood or risk for a disease or disorder caused by exposure to acetaldehyde in the subject.

In certain embodiments, the amount of 4-MP, or physiologically acceptable salt thereof, administered can be effective to increase catabolism of acetaldehyde in the subject, thereby reducing a likelihood or risk for a disease or disorder caused by exposure to acetaldehyde in the subject.

In certain embodiments, the methods comprise determining the ADH2 genotype in a subject with reduced or absent ALDH2 activity, such that the amount of 4-MP administered to the subject is appropriate to the subject's ADH2 genotype. In certain embodiments, the amount of 4-MP administered to the subject is appropriate to the ADH2 genotype determined for the subject, so as to be optimally effective in increasing catabolism of acetaldehyde in the subject.

In certain embodiments, the subject with reduced or absent ALDH2 activity who is homozygous for alcohol dehydrogenase subtype 2*1 (ADH2*1/ADH2*1) or is heterozygous for alcohol dehydrogenase subtypes 2*1 and 2*2 (ADH2*1/ADH2*2) is administered about 0.1 mg/kg to about 5 mg/kg 4-MP.

In certain embodiments, the subject with reduced or absent ALDH2 activity who is homozygous for alcohol dehydrogenase subtype 2*1 (ADH2*1/ADH2*1) or is heterozygous for alcohol dehydrogenase subtypes 2*1 and 2*2 (ADH2*1/ADH2*2) is administered about 0.1 mg/kg to about 1.0 mg/kg 4-MP.

In certain embodiments, the subject with reduced or absent ALDH2 activity who is homozygous for alcohol dehydrogenase subtype 2*2 (ADH2*2/ADH2*2) is administered about 5 mg/kg to about 10 mg/kg 4-MP.

In certain embodiments, the acetaldehyde is a product of ethanol consumption by the subject.

In certain embodiments, the disease or disorder comprises upper aerodigestive tract cancers, digestive tract cancers or breast cancer. In an additional embodiment the upper aerodigestive tract cancer comprises esophageal, oropharynx, hypopharynx, larynx, head or neck cancer. In a further embodiment the digestive cancer comprises stomach or colon cancer.

In certain embodiments, the disease or disorder comprises late-onset Alzheimer's disease, hypertension, myocardial infarction, Parkinson's disease, amyotropic lateral sclerosis, and cerebral ischemia.

7.3. Pharmaceutical Compositions

In another aspect, provided herein are pharmaceutical compositions useful for preventing, reducing or ameliorating a symptom of ethanol intolerance, or acetaldehyde accumulation, in a subject with reduced or absent aldehyde dehydrogenase subtype 2 (ALDH2) activity. Such compositions can be used in the manufacture of medicaments or formulations for the prevention, reduction or amelioration of a symptom of ethanol intolerance, or acetaldehyde accumulation, in a subject with reduced or absent ALDH2 activity.

In a further aspect, provided herein are pharmaceutical compositions useful for reducing a likelihood or risk in a subject with reduced or absent ALDH2 activity for a disease or disorder caused by consumption of ethanol. Such compositions can be used in the manufacture of medicaments or formulations for the reduction of the likelihood or risk in a subject with reduced or absent aldehyde ALDH2 activity for a disease or disorder caused by consumption of ethanol.

In certain embodiments, the subject with reduced or absent ALDH2 activity is homozygous for alcohol dehydrogenase subtype 2*1 (ADH2*1/ADH2*1) or is heterozygous for alcohol dehydrogenase subtypes 2*1 and 2*2 (ADH2*1/ADH2*2). In certain embodiments, the subject with reduced or absent ALDH2 activity is homozygous for alcohol dehydrogenase subtype 2*2 (ADH2*2/ADH2*2).

In certain embodiments, the disease or disorder caused by consumption of ethanol comprises upper aerodigestive tract cancers, digestive tract cancers or breast cancer. In an additional embodiment the upper aerodigestive tract cancer comprises esophageal, oropharynx, hypopharynx, larynx, head or neck cancer. In a further embodiment the digestive cancer comprises stomach or colon cancer. In certain embodiments, the disease or disorder caused by consumption of ethanol comprises late-onset Alzheimer's disease, hypertension, myocardial infarction, Parkinson's disease, amyotropic lateral sclerosis, and cerebral ischemia.

In certain embodiments, a pharmaceutical composition is provided comprising 4-MP, or a physiologically acceptable salt thereof, and a physiologically acceptable excipient or diluent.

Pharmaceutical compositions may take the form of powders, tablets, lozenges, granules, capsules, pills, ampoules, syrups, or fluids. In certain embodiments, the form of the composition is liquid, for example, a syrup or fluid. In certain embodiments, the form of the composition is a solid, for example, a powder, tablet or capsule.

Pharmaceutical compositions suitable for topical administration according to the present application may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

Pharmaceutical compositions suitable for oral administration according to the methods provided herein may be formulated as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

Pharmaceutical compositions suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

In certain embodiments, the pharmaceutical composition is in the form of a storage stable formulation, for example, a solid formulation suitable for oral administration, as described in Section 7.4.

In certain embodiments, the pharmaceutical composition is in the form of a unit dosage of 4-MP or a physiologically acceptable salt thereof, as described in Section 7.5.

In certain embodiments, the pharmaceutical composition can be administered orally, topically, or transdermally, as described in Section 7.6.

In certain embodiments, the pharmaceutical composition can comprise 4-MP, or a salt thereof, in combination with one or more other active agents. Additional active agents can include, for example, a vitamin, anti-oxidant, an anti-inflammatory agent including, for example, aspirin, an nonsteroid anti-inflammatory drug, an antihistamine drug, ibuprofen, and the like.

7.4. Storage Stable Formulations

The pharmaceutical compositions provided herein may be in the form of a specific formulation, for example, a solid formulation suitable for oral administration.

Accordingly, in another aspect, provided herein are formulations comprising 4-methylpyrazole (4-MP).

In certain embodiments, the formulations are storage stable. In certain embodiments, the formulations are in solid form. In certain embodiments, the formulations are suitable for oral administration.

In certain embodiments, the formulations comprise 4-MP.

In certain embodiments, the formulations comprise 4-MP, or a physiologically acceptable salt font thereof, and an excipient.

In certain embodiments, the excipient is a liquid.

In certain embodiments, the excipient is a solid.

In certain embodiments, the excipient is a polyethylene glycol. In certain embodiments, the polyethylene glycol has a total weight average molecular weight of from about 5000 to about 10,000. In certain embodiments, the excipient is PEG 8000. In certain embodiments, the formulations further comprise one or more additional excipients. In certain embodiments, the additional excipient is a surfactant. In certain embodiments, the additional excipient is selected from the group consisting of Capryol 90® and Transcutol®.

In certain embodiments, the formulations are in a solid form.

In certain embodiments, the formulations are in a solid form at temperatures of from at least 25° C. to up to about 40° C. In certain embodiments, the formulations are in a solid form when stored at temperatures of up to about 40° C. and at relative humidities of up to about 95% for at least 8 months or more.

In certain embodiments, the formulations are physically and/or chemically stable when stored at temperatures of up to about 40° C. and at relative humidities of up to about 95% for at least 8 months or more.

In certain embodiments, the formulations are provided in the unit dosage form of a capsule and are physically stable. In certain embodiments, the capsule displays no deformity, breakage, or leakage of contents when stored at room temperature for 8 months or more; when stored at room temperature and at relative humidities of up to about 60%±5% for 8 months or more; when stored at up to about 40° C. for 8 months or more; or when stored at temperatures of up to about 40° C. and relative humidities of up to about 60%±5% for 8 months or more.

In certain embodiments, the formulations are provided in the unit dosage form of a capsule and are chemically stable. In certain embodiments, the capsule retains at least about 90% content of 4-MP when stored at room temperature for 8 months or more; when stored at room temperature and at relative humidities of up to about 60%±5% for 8 months or more; when stored at temperatures of up to about 40° C. for 8 months or more; or when stored at temperatures of up to about 40° C. and at relative humidities of up to about 60%±5% for 8 months or more.

The formulations provided herein may further comprise one or more additional excipients. In certain embodiments, the one or more additional excipients may be selected from the group consisting of binders, fillers, diluents, glidants, lubricants, surfactants, emulsifying agents, disintegrants, coatings, flavors, colors, sweetening agents, preservatives, sorbents, and any other additive known to one of skill in the art.

Suitable binders may include, but are not limited to, hydroxypropyl cellulose, hydroxypropyl methyl cellulose, microcrystalline cellulose, polyvinylpyrrolidone, polyvinylpolypyrrolidone, polyethylene glycol, gum tragacanth, gelatin, and the like.

Suitable fillers and/or diluents may include, but are not limited to, lactose, glucose, sucrose, mannitol, sorbitol, calcium carbonate, calcium sulfate, calcium phosphate, hydroxypropyl cellulose, microcrystalline cellulose, silicified microcrystalline cellulose, water, ethanol, polyethylene glycol, propylene glycol, glycerol, starch, polyvinylpyrrolidone, magnesium stearate, magnesium metasilicate aluminate, and the like.

Suitable glidants may include, but are not limited to, silicon dioxide, colloidal silicon dioxide, talc, magnesium carbonate, and the like.

Suitable lubricants may include, but are not limited to, stearic acid; stearic acid metal salts such as calcium stearate or magnesium stearate; talc; colloidal silica; waxes such as beeswax; sulfates such as sodium sulfate; glycol; lauryl sulfates such as sodium lauryl sulfate or magnesium lauryl sulfate; silicates such as silicic anhydride or silicate hydrate; and the like.

Suitable surfactants may include, but are not limited to, anionic surfactants such as sodium dodecyl sulfate; cationic surfactants such as hexadecyl trimethyl ammonium bromide; amphoteric surfactants such as cocamidopropyl betaine; nonionic surfactants such as propylene glycol monocaprylate (Capryol 90®) or diethylene glycol monoethyl ether (Transcutol®); and the like.

Suitable disintegrants may include, but are not limited to, cellulose derivatives such as low-substituted hydroxypropyl cellulose, carboxymethyl cellulose, calcium carboxymethyl cellulose or internally crosslinked sodium carboxymethyl cellulose; cross-linked polyvinylpyrrolidone; and chemically modified starches/celluloses such as carboxymethyl starch, sodium carboxymethyl starch, sodium starch glycolate, pregelatinised starch or croscarmellose sodium; and the like.

Suitable coatings may include, but are not limited to, hydroxy propylmethylcellulose (HPMC), gelatin, and the like.

Suitable preservatives may include, but are not limited to, cysteine, methionine, citric acid, sodium citrate, methyl paraben, propyl paraben, and the like.

7.5. Unit Dosages

The pharmaceutical compositions and formulations provided herein may be in the form of unit dosage.

Accordingly, in another aspect, provided herein are unit dosages comprising 4-methylpyrazole (4-MP).

The unit dosage may be produced using any commonly used method well known to one of skill in the art. Examples of suitable methods include those disclosed in, for example, Ansel et al., *Pharmaceutical Dosage Forms and Drug Delivery Systems*, $6^{th}$ ed., 1995, Williams & Wilkins, Baltimore Md. For example, the unit dosage forms provided herein may be prepared by mixing particles of 4-MP, or a physiologically acceptable salt form thereof, and one or more excipients to form a bulk blend. When the bulk blend is sufficiently mixed so as to be homogenous, the composition may be readily subdivided into unit dosages, for example, tablets, pills, capsules, caplets, and the like. In the unit dosage, the 4-MP, or a physiologically acceptable salt form thereof, is included in an effective amount sufficient to produce the desired effect, for example, the desired effect of treating ethanol intolerance in the subject.

In certain embodiments, the unit dosage is in the form of a tablet.

Tablets may be prepared using any tableting technique known to one of skill in the art. For example, tablets may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. Other conventional methods such as wet granulation or dry granulation may also be used. See, for example, Ansel et al., *Pharmaceutical Dosage Forms and Drug Delivery Systems*, 1995, $6^{th}$ ed., Williams & Wilkins, Baltimore Md., pp. 182-222.

In certain embodiments, the unit dosage is in the form of a capsule.

Capsules may be prepared using any capsule-filling technique known to one of skill in the art. For example, capsules may be prepared by transferring the bulk blend directly to a capsule filling and sealing machine, as described in, for example, U.S. Pat. Nos. 6,834,475 and 7,082,738. See also, for example, Ansel et al., *Pharmaceutical Dosage Forms and Drug Delivery Systems*, 1995, $6^{th}$ ed., Williams & Wilkins, Baltimore Md., pp. 164-182.

The capsules may be comprised of gelatin, plasticized gelatin, hydroxypropylmethylcellulose (HPMC), starch or agar, or any other material known to one of skill in the art.

In certain embodiments, the capsule comprises gelatin. In certain embodiments, the capsule comprises soft gelatin. In certain embodiments, the capsule comprises hard gelatin.

Plasticizers may be added to the capsule material to increase the flexibility and strength and may be selected from glycerin, propylene glycol, polyethylene glycol, triethyl citrate, acetyl triethyl citrate, diethyl phthalate, dibutyl phthalate, dibutyl sebacate, or mixtures thereof, or any other material or mixture known to one of skill in the art. The plasticizer may be present in an amount ranging from 0.1% to 30% by weight of the capsule.

The capsules may be sized to hold the desired amount of the formulation, typically up to about 0.50 ml of formulation. Preferably, the size of any particular capsule described herein will correspond to a conventional capsule size, e.g. Size Nos. 00, 0, 1, 2, 3, 4, 5, and the like. See, for example, Remington's *The Science and Practice of Pharmacy*, 2005, 21$^{st}$ ed.

The tablets and capsules may also be coated with an enteric coating, alone or in addition to another coating. See, for example, Remington's *The Science and Practice of Pharmacy*, 2005, 21$^{st}$ ed.

Materials suitable for use in the enteric coating include hydroxypropyl methylcellulose, hydroxyethyl cellulose, hydroxypropyl cellulose, methylcellulose, ethylcellulose, acrylic acid methacrylic acid ester copolymer, or a mixture thereof.

Additional materials suitable for use in the enteric coating include phthalates including hydroxypropyl methylcellulose phthalate, hydroxyethyl cellulose phthalate, hydroxypropyl cellulose phthalate, methylcellulose phthalate, ethylcellulose phthalate, and cellulose acetate phthalate.

The tablets and capsules may additionally be coated with a controlled release coating, which is compatible with the other components of the enteric coating. The controlled release coating may comprise a hydrophobic controlled release material selected from an alkylcellulose, an acrylic polymer, or mixtures thereof.

The controlled release coatings may also include a plasticizer such as those described herein.

In certain embodiments, the unit dosages provided herein comprise different amounts of 4-MP.

In certain embodiments, the unit dosages comprise about 0.05 mg; about 0.1 mg; about 0.5 mg; about 1 mg; about 1.5 mg; about 2 mg; about 2.5 mg; about 3 mg; about 3.5 mg; about 4 mg; about 4.5 mg; or about 5 mg 4-MP.

In certain embodiments, the unit dosages comprise about 5 mg; about 6 mg; about 7 mg; about 8 mg; about 9 mg; about 10 mg; about 15 mg; about 20 mg; or about 50 mg 4-MP.

In certain embodiments, the unit dosages comprise about 50 mg; about 60 mg; about 70 mg; about 80 mg; about 90 mg; about 100 mg; about 150 mg; about 200 mg; or about 500 mg 4-MP.

In certain embodiments, the unit dosages comprise about 0.05 to about 5 mg; about 0.1 to about 5 mg; about 0.5 to about 5 mg; about 1.0 to about 5 mg; about 0.5 to about 4 mg; about 0.5 to about 3 mg; about 0.5 to about 2 mg; about 0.5 to about 1 mg; about 1 to about 2 mg; about 2.0 to about 3 mg; about 3 to about 4 mg; or about 4 to about 5 mg 4-MP.

In certain embodiments, the unit dosages comprise about 5 to about 50 mg; about 10 to about 50 mg; about 5 to about 6 mg; about 6 to about 7 mg; about 7 to about 8 mg; about 8 to about 9 mg; about 9 to about 10 mg; about 10 to about 15 mg; about 15 to about 20 mg; or about 20 to about 50 mg 4-MP.

In certain embodiments, the unit dosages comprise about 50 to about 500 mg; about 100 to about 500 mg; about 50 to about 60 mg; about 60 to about 70 mg; about 70 to about 80 mg; about 80 to about 90 mg; about 90 to about 100 mg; about 100 to about 150 mg; about 150 to about 200 mg; or about 200 to about 500 mg 4-MP.

In another aspect, provided herein are hard gelatin capsules encapsulating 4-MP, or a physiologically acceptable salt form thereof, and an excipient.

In certain embodiments, the excipient in the capsule is a polyethylene glycol. In certain embodiments, the polyethylene glycol has a total weight average molecular weight of from about 5000 to about 10,000. In certain embodiments, the excipient in the capsule is PEG 6000 or PEG 8000.

In certain embodiments, the capsule retains physical integrity when stored at temperatures of up to about 55° C. for at least 8 months or more; when stored at temperatures of up to about 40° C. and at relative humidities of up to about 95% for at least 8 months or more; or when stored at room temperature and at relative humidities of up to about 60%±5% for 8 months or more.

In certain embodiments, the contents of the capsule are in solid form. In certain embodiments, the contents of the capsule are in solid form at temperatures of up to about 40° C. and at relative humidities of up to about 95% for at least 8 months or more; or at room temperature and at relative humidities of up to about 60%±5% for 8 months or more.

7.6. Methods of Administration

In another aspect, provided herein are methods of administration of the compositions and formulations provided herein.

The compositions and formulations provided herein can be administered according to any technique known to one of skill in the art. In preferable embodiments, the subject can self-administer the composition or formulation to himself or herself.

In certain embodiments, the composition or formulation can be administered topically.

In certain embodiments, the composition or formulation can be administered transdermally.

In certain embodiments, the composition or formulation can be administered orally. When orally administered, the composition or formulation can be in a solid form. When orally administered, the formulations can also be in a unit dosage form, for example, as in a tablet, capsule and the like, as provided herein.

The composition or formulation can be administered alone or in combination with other substances or active agents. In some embodiments, a formulation and other ingredients, as described below, is administered.

In certain embodiments, the amount of 4-MP administered in the formulation can be between about 0.1 mg/kg to about 5 mg/kg. In certain embodiments, the amount of 4-MP administered in the formulation can be between about 0.1 mg/kg to about 4 mg/kg. In certain embodiments, the amount of 4-MP administered in the formulation can be between about 0.1 mg/kg to 1.0 mg/kg. In certain embodiments, the amount of 4-MP administered in the formulation can be between about 0.5 mg/kg to 1.0 mg/kg. In certain embodiments, the amount of 4-MP administered in the formulation can be between about 1.0 mg/kg to about 5 mg/kg. In certain embodiments, the amount of 4-MP administered in the formulation can be between about 1.0 mg/kg to about 4 mg/kg. In certain embodiments, the amount of 4-MP administered in the formulation can be between about 1.0 mg/kg to 2 mg/kg. As will be understood by one of skill in the art, the amounts of 4-MP to be administered in the formulation, as described herein, are based on the body mass of the subject, expressed in kilograms. In certain embodiments, about 0.05 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.5 mg/kg, about 2 mg/kg, about 2.5 mg/kg, about 3 mg/kg, about 3.5 mg/kg, about 4 mg/kg, about 4.5 mg/kg, or about 5 mg/kg of 4-MP are administered to the subject in the formulation. In certain embodiments, the amount of 4-MP administered in the formulation can be in the range between about 0.05 mg/kg to about 0.1 mg/kg; between about 0.1 mg/kg to about 5 mg/kg; between about 0.1 mg/kg to about 4 mg/kg; between about 0.1 mg/kg to about 1.0 mg/kg; between about 0.5 mg/kg to about 1.0 mg/kg; between about 1.0 mg/kg to about 5 mg/kg; between about 1.0 mg/kg to about 4 mg/kg; or between about 1.0 mg/kg to about 2 mg/kg.

In certain embodiments, the amount of 4-MP administered in the formulation can be between about 0.1 mg/kg to about 10 mg/kg. In certain embodiments, the amount of 4-MP administered in the formulation can be between about 1.0 mg/kg to about 10 mg/kg. In certain embodiments, the amount of 4-MP administered in the formulation can be between about 5 mg/kg to 10 mg/kg. In certain embodiments, about 5 mg/kg, about 6 mg/kg, about 7 mg/kg, about 8 mg/kg, about 9 mg/kg, or about 10 mg/kg of 4-MP are administered to the subject in the formulation. In certain embodiments, the amount of 4-MP administered in the formulation can be in the range between about 0.1 mg/kg to about 10 mg/kg; between about 1.0 mg/kg to about 10 mg/kg; or between about 5 mg/kg to about 10 mg/kg.

In certain embodiments, the formulations provided herein are suitable for administration to subjects wishing to reduce or ameliorate a symptom of ethanol intolerance or acetaldehyde accumulation. In certain embodiments, the subject has reduced or absent ALDH2 activity, as described in Goedde et al., *Hum. Genet.* 1992, 88, 344-346, and Xiao et al., *J. Clin. Invest.* 1995, 96, 2180-2186. In certain embodiments, the subject is also a carrier for the ADH2*2 allele, which is associated with the accumulation of acetaldehyde (Crabb et al., *Proc. Nutr. Soc.* 2004, 63(1), 49-63). Symptoms of ethanol intolerance, or acetaldehyde accumulation, may include, but are not limited to, flushing, elevated heart rate, palpitations, hypotension, nausea, dizziness, headache, vomiting, diarrhea, upset stomach, ataxia, or confused consciousness. See, for example, Ward et al., *Alcohol and Alcoholism* 1994, 29, 433-438. In certain embodiments, the subject is a human.

In certain embodiments, the ALDH2 and ADH2 genotypes of the subject are determined prior to administration of 4-MP. In certain embodiments, the ALDH2 genotype of the subject is determined prior to administration of 4-MP. In certain embodiments, the ADH2 genotype of the subject is determined prior to administration of 4-MP.

In certain embodiments, the methods comprise determining the ADH2 genotype in a subject with reduced or absent ALDH2 activity, such that the amount of 4-MP administered to the subject is appropriate for the subject's determined ADH2 genotype.

In certain embodiments, the subject with reduced or absent ALDH2 activity who is homozygous for alcohol dehydrogenase subtype 2*1 (ADH2*1/ADH2*1) or is heterozygous for alcohol dehydrogenase subtypes 2*1 and 2*2 (ADH2*1/ADH2*2) is administered about 0.1 mg/kg to about 5 mg/kg 4-MP.

In certain embodiments, the subject with reduced or absent ALDH2 activity who is homozygous for alcohol dehydrogenase subtype 2*1 (ADH2*1/ADH2*1) or is heterozygous for alcohol dehydrogenase subtypes 2*1 and 2*2 (ADH2*1/ADH2*2) is administered about 0.1 mg/kg to about 1.0 mg/kg 4-MP.

In certain embodiments, the subject with reduced or absent ALDH2 activity who is homozygous for alcohol dehydrogenase subtype 2*2 (ADH2*2/ADH2*2) is administered about 5 mg/kg to about 10 mg/kg 4-MP.

In certain embodiments, the formulation can be administered before the subject has consumed ethanol. In certain embodiments, the formulation can be administered about one minute, about fifteen minutes, or about one hour before the subject consumes ethanol. In certain embodiments, the formulation can be orally administered about two hours to about fifteen minutes before the subject consumes ethanol.

In certain embodiments, the formulation can be administered concurrent with the consumption of ethanol. In certain embodiments, the formulation can be administered immediately before or after the consumption of ethanol. In certain embodiments, the formulation can be administered to a subject after the subject has consumed ethanol.

In certain embodiments, the amount of 4-MP, or physiologically acceptable salt thereof, administered in the formulation can be effective to reduce acetaldehyde accumulation by about 50% to about 60% in a subject as compared to when the formulation is not administered to the subject. In certain embodiments, the peak acetaldehyde accumulation can be effectively eliminated or reduced by about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, or about 5%.

In certain aspects, methods are provided for preventing a disease associated with the long term use of ethanol in a subject. In general, diseases associated with the long term use of ethanol include, for example and without limitation, liver cirrhosis and cancer, for example, hepatocellular carcinoma, mouth cancer, stomach cancer, and esophageal cancer.

In certain embodiments, provided herein are methods for preventing a disease associated with the long term use of ethanol in a subject, 4-MP is administered prior to the consumption of ethanol by the subject. In some embodiments, 4-MP can be administered within about two hours before the subject consumes ethanol.

8. EXAMPLES

8.1. Elimination of Ethanol Versus Dose of 4-MP

The example below demonstrates that with certain doses of 4-MP contemplated herein, the percent reduction in ethanol elimination rate can be negligibly or minimally impacted.

Without intending to be bound by any particular theory of operation, it is believed that when 4-MP in doses of about 4 mg/kg or less are administered to a human subject, the reduction in the elimination of ethanol consumed by the subject will be less than about 10%. FIG. 2 provides a graph of data representing amounts of 4-MP per kilogram body weight administered to human subjects versus observed percent reduction in ethanol elimination rates were obtained from the following sources and the averages determined as indicated in parenthesis: Lindros et al., *Alcoholism: Clinical and Experimental Research* 1981, 5, 528-530 (6 mg 4-MP; 20% reduction in EtOH elimination); Inoue et al., *Alcoholism: Clinical and Experimental Research*, 1984, 8, 319-322 (10 mg 4-MP; 20% reduction in EtOH elimination); Inoue et al., *Japan. J. Pharmacol.* 1985, 38, 43-48 (8.5 mg 4-MP; 12% reduction in EtOH elimination); Sarkola et al., *Alcoholism: Clinical and Experimental Research*, 2002, 26, 239-245 (12.5 mg 4-MP; 34% reduction in EtOH elimination). The data was plotted and linear least squares regression was used to fit a line to the data. The plot indicates that for doses of 4 mg/kg 4-MP and less, the ethanol elimination rate will be minimally impacted, i.e., that the reduction in ethanol elimination will be less than about 10%.

8.2. Reducing Acetaldehyde Concentration in Human Subjects Expressing Specific Polymorphisms of the ALDH2 and ADH2 Genes The example below demonstrates that 4-MP works to reduce acetaldehyde accumulation accompanying ethanol consumption in human subjects expressing specific polymorphisms of the ALDH2 and ADH2 genes.

8.2.1 Methods

A blinded, intra-subject controlled, single dose, dose escalation study of 4-MP for mitigation of acetaldehyde related toxicity in subjects with symptoms of inborn altered ethanol metabolism with concomitant ethanol exposure was undertaken.

Thirty-two (n=32) healthy human subjects of Japanese descent, 21 to 50 years of age, known to have intolerance to ethanol due to a history of flushing, heart palpitations, and/or nausea following ethanol consumption, and exhibiting a positive result to a skin ethanol patch test, were selected for the study population.

Twenty-four subjects (n=24) were randomly selected and orally administered 1 mg/kg, 3 mg/kg, or 5 mg/kg of 4-MP, followed 30 minutes later by an oral dose of 20% ethanol (5 mg/kg). The dosing protocol is shown in Table 1.

TABLE 1

Dosing protocol for 4-MP

| 4-MP Dose | 4-MP then ETOH | ETOH then 4-MP |
|---|---|---|
| 1 mg/kg | 12 subjects | 4 subjects |
| 3 mg/kg | 4 subjects | 4 subjects |
| 5 mg/kg | 8 subjects | |

Using the same protocol, wherein 4-MP was replaced with placebo, each of the twenty-four randomly selected subjects served as its own control.

The twenty-four randomly selected subjects were then subjected to blood sampling, and the sampled blood analyzed for acetaldehyde levels at select time points following ethanol consumption.

For acetaldehyde analysis, blood samples were prepared by dilution with an internal standard (acetaldehyde-d4), with derivatization of acetaldehyde with dinitrophenyl hydrazine in hydrochloric acid, liquid-liquid portioning and solvent exchange. The derivatization forms an acetaldehyde-dinitrophenyl hydrazine (DNPH) derivative which dramatically increases the boiling point of the molecule and thus its relative stability compared to the acetaldehyde itself (Nagy et al., *Rapid Communications in Mass Spectrometry* 2004, 18, 2473-2478). The derivatized analytes were separated using a Jones Chromatography (Grace-Vydac), 50 mm×2.1 mm, 3 µm column held in an oven set at 28° C. Two mobile phases were used in a gradient consisting of 30:70 acetonitrile:water versus 90:10 acetonitrile:water with 0.1% formic acid. The derivatized analyte was detected on a High Performance Liquid Chromatograph equipped with a Mass Spectrometer (HPLC/MS/MS). Quantitation was performed using a linear regression curve fit of impurities standards with 1/x weighting, prepared from dilutions of acetaldehyde in water. Samples and standards were injected at 2 µL.

All thirty-two subjects were then genotyped for ALDH2 and ADH2 at the Alcohol Research Center at Indiana University using (i) genomic DNA isolation and (ii) TaqMan assay for allelic discrimination.

i. Genomic DNA isolation: DNA was first isolated using the "HotSHOT" method for isolating PCR quality genomic DNA (Truett et al., *Biotechniques* 2000, 29(1), 52-54). Briefly, blood blotted on filter paper (3 mm circle) was placed in the well of a 96-well plate and mixed with 75 µL 25 mM NaOH/0.3 mM EDTA solution and heated to 95° C. for 40 minutes, followed by neutralization with 75 µL 40 mM Tris-HCl (pH 5) solution. 1-5 microliters were used for each PCR.

ii. TaqMan Assay for Allelic Discrimination: The allelic discrimination assay used a multiplexed (more than one primer/probe pair per reaction), end-point (data is collected at the end of the PCR process) assay. Each assay mix contained two different TaqMan probes (Applied BioSystems, Foster City, Calif.), labeled with VIC or FAM fluorescent reporter dye, which bound preferentially to one of the alleles. The genotype of each sample was determined by the fluorescence levels of the reporter dyes and was clustered on a graph with other samples of the same genotype. Each reaction contained 5 µL of 2×TaqMan Universal PCR Masternix, No AmpErase UNG, 3.75 µL of water, 0.25 µL of 40× Assay Mix, and 1 µL of DNA sample. Eight or eleven controls were included on each 96-well plate: two no template controls, two or three heterozygous samples, and two or three of each of the homozygous samples. Thermocycling was carried out in MJ Research PTC-200 thermocyclers. The PCR products were then analyzed in an ABI PRISM® 7300 Sequence Detection System (SDS) instrument. SDS Software 1.3.1 converted the raw data to pure dye components and plotted the results of the allelic discrimination on a scatter plot of Allele X versus Allele Y (e.g., ADH2*1 versus ADH2*2); each genotype appeared on the graph as a cluster of points.

On the basis of the ALDH2 and ADH2 genotyping described above, subjects were found to fall into seven genotypic groups (Groups A, B, C, D, E, F and G):

Group A: heterozygous for aldehyde dehydrogenase subtypes 2*1 and 2*2 (ALDH2*1/ALDH2*2), and homozygous for alcohol dehydrogenase subtype 2*1 (ADH2*1/ADH2*1); there were two subjects (n=2) in this group;

Group B: homozygous for aldehyde dehydrogenase subtype 2*2 (ALDH2*2/ALDH2*2), and homozygous for alcohol dehydrogenase subtype 2*1 (ADH2*1/ADH2*1); there was one subject (n=1) in this group;

Group C: homozygous for aldehyde dehydrogenase subtype 2*1 (ALDH2*1/ALDH2*1), and heterozygous for alcohol dehydrogenase subtypes 2*1 and 2*2 (ADH2*1/ADH2*2); there were four subjects (n=4) in this group;

Group D: heterozygous for aldehyde dehydrogenase subtypes 2*1 and 2*2 (ALDH2*1/ALDH2*2), and heterozygous for alcohol dehydrogenase subtypes 2*1 and 2*2 (ADH2*1/ADH2*2); there were six subjects (n=6) in this group;

Group E: homozygous for aldehyde dehydrogenase subtype 2*1 (ALDH2*1/ALDH2*1), and homozygous for alcohol dehydrogenase subtype 2*2 (ADH2*2/ADH2*2); there were five subjects (n=5) in this group;

Group F: heterozygous for aldehyde dehydrogenase subtypes 2*1 and 2*2 (ALDH2*1/ALDH2*2), and homozygous for alcohol dehydrogenase subtype 2*2 (ADH2*2/ADH2*2); there were thirteen subjects (n=13) in this group; and Group G: homozygous for aldehyde dehydrogenase subtype 2*2 (ALDH2*2/ALDH2*2), and homozygous for alcohol dehydrogenase subtype 2*2 (ADH2*2/ADH2*2); there was one subject (n=1) in this group.

Table 2 indicates the ADLH2 and ADH2 genotype of each of the thirty-two subjects.

TABLE 2

ADLH2 and ADH2 genotype of study subjects

| | ADH2*1/ADH2*1 Normal ADH2 activity | ADH2*1/ADH2*2 Enhanced ADH2 activity | ADH2*2/ADH2*2 "Superactive" ADH2 |
|---|---|---|---|
| ALDH2*1/ALDH2*1 Normal ALDH2 activity | | Group C (4 subjects) | Group E (5 subjects) |
| ALDH2*1/ALDH2*2 Reduced ALDH2 activity | Group A (2 subjects) | Group D (6 subjects) | Group F (13 subjects) |
| ALDH2*2/ALDH2*2 Absent ALDH2 activity | Group B (1 subject) | | Group G (1 subject) |

Data pertaining to acetaldehyde concentrations measured from the blood samples of subjects from each of the seven groups described above were compared as a function of genotype.

8.2.2 Results 8.2.2.1 Groups A and D

FIG. 3 presents a graph of mean serum acetaldehyde concentration measured in six subjects (n=6) with reduced ALDH2 activity, who are also ADH2*1/ADH2*1 homozygous or ADH2*1/ADH2*2 heterozygous (Groups A and D), following dosage with 1 mg/kg 4-MP, and comparison with placebo.

Table 3 presents the pharmacokinetic parameters of "$C_{max}$ mean" and "$AUC_{0-8H}$ mean" calculated from the data presented in FIG. 3 using standard mathematical models known to those of skill in the art. P-values and standard errors were determined from statistical analysis of the data and are also presented in Table 3.

TABLE 3

$C_{max}$ mean and $AUC_{0-8\,H}$ mean calculated from the data presented in FIG. 3

| | 4-MP (n = 6) | Placebo (n = 6) | P-value |
|---|---|---|---|
| $C_{max}$ mean (μg/ml) (SE) | 41.3 (5.2) | 64.7 (8.4) | 0.029 |
| Acetaldehyde $AUC_{0-8\,H}$ mean (μg * hr/mL) (SE) | 162 (18.7) | 186 (14.8) | 0.071 |

FIG. 3 demonstrates that the peak mean acetaldehyde concentration in the blood due to drinking ethanol can be reduced in subjects with reduced ALDH2 activity, who are also ADH2*1/ADH2*1 homozygous or ADH2*1/ADH2*2 heterozygous, following administration with 1 mg/kg 4-MP.

Table 3 demonstrates that the $C_{max}$ mean and $AUC_{0-8H}$ mean of acetaldehyde concentration in the blood due to drinking ethanol can be significantly reduced in subjects with reduced ALDH2 activity, who are also ADH2*1/ADH2*1 homozygous or ADH2*1/ADH2*2 heterozygous, following administration with 1 mg/kg 4-MP, relative to the $C_{max}$ mean and $AUC_{0-8H}$ mean in those subjects after drinking ethanol in the absence of 4-MP. For example, according to Table 3, $C_{max}$ mean is reduced from 64.7±8.4 μg/mg to 41.3±5.2 μg/mg, and $AUC_{0-8H}$ mean is reduced from 186±14.8 μg*hr/mL to 162±18.7 μg*hr/mL, relative to placebo. The reduction in $C_{max}$ mean represents a reduction of approximately 36%.

These results demonstrate that 1 mg/kg 4-MP is effective in reducing acetaldehyde accumulation accompanying ethanol consumption in subjects with reduced ALDH2 activity, for example, those subjects who are also ADH2*1/ADH2*1 homozygous or ADH2*1/ADH2*2 heterozygous.

8.2.2.2 Groups F and G

FIG. 4 presents a graph of mean serum acetaldehyde concentration measured in six subjects (n=6) with reduced or absent ALDH2 activity, who are also ADH2*2/ADH2*2 homozygous (Groups F and G), following dosage with 1 mg/kg 4-MP, and comparison with placebo.

Table 4 presents the pharmacokinetic parameters of "$C_{max}$ mean" and "$AUC_{0-8H}$ mean" calculated from the data presented in FIG. 4 using standard mathematical models known to those of skill in the art. P-values and standard errors were determined from statistical analysis of the data and are also presented in Table 4.

TABLE 4

$C_{max}$ mean and $AUC_{0-8\,H}$ mean calculated from the data presented in FIG. 4

| | 4-MP (n = 6) | Placebo (n = 6) | P-value |
|---|---|---|---|
| $C_{max}$ mean (μg/ml) (SE) | 89.2 (10.0) | 83.2 (8.4) | 0.351 |
| Acetaldehyde $AUC_{0-8\,H}$ mean (μg * hr/mL) (SE) | 221 (11.6) | 206 (30.0) | 0.338 |

FIG. 4 demonstrates that the peak mean acetaldehyde concentration in the blood due to drinking ethanol is not reduced in subjects with reduced or absent ALDH2 activity, who are also ADH2*2/ADH2*2 homozygous, following administration with 1 mg/kg 4-MP.

Table 4 demonstrates that the $C_{max}$ mean and $AUC_{0-8H}$ mean of acetaldehyde concentration in the blood due to drinking ethanol is not significantly reduced in subjects with reduced or absent ALDH2 activity, who are also ADH2*2/ADH2*2 homozygous, following administration with 1 mg/kg 4-MP, relative to the $C_{max}$ mean and $AUC_{0-8H}$ mean in those subjects after drinking ethanol in the absence of 4-MP.

These results indicate that certain subjects with reduced or absent ALDH2 activity, for example, those subjects who are also ADH2*2/ADH2*2 homozygous, are less likely to be benefited by administration of certain doses of 4-MP, for example, 1 mg/kg 4-MP. This result indicates the presence of a differential response to the administration of 4-MP in alcohol intolerant human subjects.

8.2.2.3 Groups A, B, D, F and G

FIG. 5 presents a graph of mean serum acetaldehyde concentration across twenty-three subjects (n=23) with reduced or absent ALDH2 activity (Groups A, B, D, F and G), following dosage with 1 mg/kg, 3 mg/kg or 5 mg/kg 4-MP, and comparison with placebo.

Table 5 presents the pharmacokinetic parameters of "$C_{max}$ mean" and "$AUC_{0-8H}$ mean" calculated from the data presented in FIG. 5 using standard mathematical models known to those of skill in the art. P-values and standard errors were determined from statistical analysis of the data and are also presented in Table 5.

TABLE 5

$C_{max}$ mean and $AUC_{0-8\,H}$ mean calculated from the data presented in FIG. 5

| | 4-MP (n = 23) | Placebo (n = 23) | P-value |
|---|---|---|---|
| $C_{max}$ mean (μg/ml) (SE) | 64.2 (7.0) | 66.6 (6.3) | 0.367 |

TABLE 5-continued $C_{max}$ mean and $AUC_{0-8\,H}$ mean calculated from the data presented in FIG. 5

|  | 4-MP (n = 23) | Placebo (n = 23) | P-value |
|---|---|---|---|
| Acetaldehyde $AUC_{0-8\,H}$ mean (μg * hr/mL) (SE) | 182 (10.5) | 188 (13.5) | 0.307 |

FIG. 5 demonstrates that the peak mean acetaldehyde concentration in the blood due to drinking ethanol is not reduced across all subjects with reduced or absent ALDH2 activity, following administration with 1 mg/kg, 3 mg/kg or 5 mg/kg 4-MP.

Table 5 demonstrates that the $C_{max}$ mean and $AUC_{0-8H}$ mean of acetaldehyde concentration in the blood due to drinking ethanol is not significantly reduced in all subjects with reduced or absent ALDH2 activity, following administration with 1 mg/kg, 3 mg/kg or 5 mg/kg 4-MP, relative to the $C_{max}$ mean and $AUC_{0-8H}$ mean in those subjects after drinking ethanol in the absence of 4-MP.

These results indicate that certain subjects with reduced or absent ALDH2 activity, for example, those subjects who are also ADH2*2/ADH2*2 homozygous, are less likely to be benefited by administration of doses of 4-MP within the range of 1-5 mg/kg.

Taken together, the above studies indicate the presence of a differential response to the administration of 4-MP in alcohol intolerant human subjects: certain alcohol intolerant human subjects, for example, subjects with reduced ALDH2 activity who are also ADH2*1/ADH2*1 homozygous or ADH2*1/ADH2*2 heterozygous, are more likely to be benefited by the administration of 4-MP within the range of 1-5 mg/kg than other subpopulations of alcohol intolerant human subjects, for example, subjects with reduced ALDH2 activity who are also ADH2*2/ADH2*2 homozygous.

8.3. Exemplary Administration of 4-MP to a Human Subject

The example below describes exemplary administration of 4-MP to a human subject.

4-MP in its free base, liquid form, is mixed with orange juice to make a 0.5% (w/v) 4-MP solution. The 4-MP may be stored in a container with an associated dispensing cup with markings indicating various amounts of solution to be used for different body masses of people to whom the 4-MP will be administered. For a person with a body mass of about 75 kg with reduced or absent ALDH2 activity who will be drinking ethanol, about 60 milliliters of the 4-MP is poured into the dispensing cup and the person with reduced or absent ALDH2 can drink the 4-MP solution from the cup in the minutes or hours prior to drinking alcohol.

8.4. Exemplary Genotyping of Human Subject and Administration of Amount of 4-MP Appropriate to Genotype The example below describes exemplary determination of the ALDH2 and ADH2 genotypes of a human subject and administration of an amount of 4-MP appropriate to the determined genotype.

The ALDH2 and ADH2 genotypes of the subject are determined prior to administration of 4-MP. The human subject is ALDH2 and ADH2 genotyped using methods such as those described in Section 8.2. Based on the ALDH2 and ADH2 genotyping, subjects are predicted to fall into nine genotypic groups (Groups 1, 2, 3, 4, 5, 6, 7, 8 and 9):

Group 1: homozygous for aldehyde dehydrogenase subtype 2*1 (ALDH2*1/ALDH2*1), and homozygous for alcohol dehydrogenase subtype 2*1 (ADH2*1/ADH2*1);

Group 2: heterozygous for aldehyde dehydrogenase subtypes 2*1 and 2*2 (ALDH2*1/ALDH2*2), and homozygous for alcohol dehydrogenase subtype 2*1 (ADH2*1/ADH2*1);

Group 3: homozygous for aldehyde dehydrogenase subtype 2*2 (ALDH2*2/ALDH2*2), and homozygous for alcohol dehydrogenase subtype 2*1 (ADH2*1/ADH2*1);

Group 4: homozygous for aldehyde dehydrogenase subtype 2*1 (ALDH2*1/ALDH2*1), and heterozygous for alcohol dehydrogenase subtypes 2*1 and 2*2 (ADH2*1/ADH2*2);

Group 5: heterozygous for aldehyde dehydrogenase subtypes 2*1 and 2*2 (ALDH2*1/ALDH2*2), and heterozygous for alcohol dehydrogenase subtypes 2*1 and 2*2 (ADH2*1/ADH2*2);

Group 6: homozygous for aldehyde dehydrogenase subtype 2*2 (ALDH2*2/ALDH2*2), and heterozygous for alcohol dehydrogenase subtypes 2*1 and 2*2 (ADH2*1/ADH2*2);

Group 7: homozygous for aldehyde dehydrogenase subtype 2*1 (ALDH2*1/ALDH2*1), and homozygous for alcohol dehydrogenase subtype 2*2 (ADH2*2/ADH2*2);

Group 8: heterozygous for aldehyde dehydrogenase subtypes 2*1 and 2*2 (ALDH2*1/ALDH2*2), and homozygous for alcohol dehydrogenase subtype 2*2 (ADH2*2/ADH2*2); and Group 9: homozygous for aldehyde dehydrogenase subtype 2*2 (ALDH2*2/ALDH2*2), and homozygous for alcohol dehydrogenase subtype 2*2 (ADH2*2/ADH2*2).

Table 6 indicates nine predicted genotypic groups based on the above-described ALDH2 and ADH2 genotyping. A subject whose ALDH2 and ADH2 genotype falls within any one of groups 2, 3, 5, 6, 8 and 9 (bottom two rows of the table) is considered to have reduced or absent ALDH2 activity, as defined herein.

TABLE 6

ADLH2 and ADH2 genotypic groups

|  | ADH2*1/ADH2*1 Normal ADH2 activity | ADH2*1/ADH2*2 Enhanced ADH2 activity | ADH2*2/ADH2*2 "Superactive" ADH2 |
|---|---|---|---|
| ALDH2*1/ALDH2*1 Normal ALDH2 activity | Group 1 | Group 4 | Group 7 |
| ALDH2*1/ALDH2*2 Reduced ALDH2 activity | Group 2 | Group 5 | Group 8 |
| ALDH2*2/ALDH2*2 Absent ALDH2 activity | Group 3 | Group 6 | Group 9 |

Once the human subject is genotyped as described above, the amount of 4-MP administered to the subject may be advantageously tailored to the determined genotype, so as to be optimally effective in reducing or inhibiting the ethanol-oxidizing activity of the ADH2 enzyme in the subject, or so as to be optimally effective in increasing catabolism of acetaldehyde in the subject. For example, a subject falling within any one of groups 2, 3, 5 and 6 (i.e., a subject with reduced or absent ALDH2 activity who is homozygous for alcohol dehydrogenase subtype 2*1 (ADH2*1/ADH2*1) or is heterozygous for alcohol dehydrogenase subtypes 2*1 and 2*2 (ADH2*1/ADH2*2)) may administered an amount of 4-MP of about 0.1 mg/kg to 5 mg/kg. A subject falling within any one of groups 8 and 9 (i.e., a subject with reduced or absent ALDH2 activity who is homozygous for the "superactive" alcohol dehydrogenase subtype 2*2 (ADH2*2/ADH2*2)) may administered an amount of 4-MP of about 5 mg/kg to 10 mg/kg 4-MP.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

All publications and patent applications cited in this specification are herein incorporated by reference as if each individual publication or patent application were specifically and individually indicated to be incorporated by reference.

It is claimed:

1. A method for ameliorating a symptom of ethanol intolerance in a subject with reduced or absent aldehyde dehydrogenase subtype 2 (ALDH2) activity comprising orally administering to the subject about 0.1 mg to about 1.0 mg 4-methylpyrazole (4-MP) or a physiologically acceptable salt thereof per kilogram of the subject's body mass, wherein the subject is homozygous for alcohol dehydrogenase subtype 2*1 (ADH2*1/ADH2*1) or is heterozygous for alcohol dehydrogenase subtypes 2*1 and 2*2 (ADH2*1/ADH2*2).

2. The method of claim 1, wherein the symptom of ethanol intolerance is selected from the group consisting of flushing, elevated heart rate, palpitations, hypotension, nausea, dizziness, headache, vomiting, diarrhea, upset stomach, ataxia, and confused consciousness.

3. The method of claim 1, wherein 4-MP is administered in a free base form or a physiologically acceptable salt form.

4. The method of claim 1, wherein 4-MP is orally administered before the subject consumes ethanol.

5. The method of claim 4, wherein 4-MP is orally administered about one hour to about fifteen minutes before the subject consumes ethanol.

6. The method of claim 1, wherein 4-MP is orally administered concurrently with the subject's consumption of ethanol or after the subject has consumed ethanol.

7. The method of claim 1, wherein the percent reduction in the subject's ethanol elimination rate is no more than about 10% in comparison to the ethanol elimination rate of a subject not administered 4-MP.

8. A method of reducing or ameliorating a symptom associated with acetaldehyde accumulation accompanying ethanol consumption in a subject with reduced or absent aldehyde dehydrogenase subtype 2 (ALDH2) activity comprising administering
   i) an effective amount of 4-MP that reduces acetaldehyde accumulation by about 50% to about 60% as compared to a subject not administered 4-MP, wherein about 0.1 mg to about 1.0 mg 4-MP per kilogram of the subject's body mass is administered; or
   ii) an amount of 4-MP or a physiologically acceptable salt of 4-MP effective to reduce or inhibit ethanol-oxidizing activity of alcohol dehydrogenase in the subject, wherein about 0.1 mg to about 1.0 mg 4-MP per kilogram of the subject's body mass is administered,
   wherein the subject with reduced or absent ALDH2 activity is homozygous for alcohol dehydrogenase subtype 2*1 (ADH2*1/ADH2*1) or is heterozygous for alcohol dehydrogenase subtypes 2*1 and 2*2 (ADH2*1/ADH2*2).

9. The method of claim 8, wherein a symptom of acetaldehyde accumulation is selected from the group consisting of flushing, elevated heart rate, palpitations, hypotension, nausea, dizziness, headache, vomiting, diarrhea, upset stomach, ataxia, and confused consciousness.

10. The method of claim 8, wherein the percent reduction in ethanol elimination rate that is no more than about 10% in comparison to the ethanol elimination rate of a subject not administered 4-MP.

11. The method of claim 8, wherein an effective amount of a hydrochloride salt of 4-MP is administered.

12. The method of claim 1, wherein about 1.0 mg 4-MP per kilogram of the subject's body mass is administered.

13. The method of claim 1, wherein about 0.5 mg 4-MP per kilogram of the subject's body mass is administered.

14. The method of claim 1, wherein the subject is a human.

15. A method for ameliorating a symptom of ethanol intolerance in a subject comprising orally administering to the subject about 0.1 mg to about 1.0 mg 4-methylpyrazole (4-MP) or a physiologically acceptable salt thereof per kilogram of the subject's body mass, wherein the subject has the following genotype:
   i) ADH2*1/ADH2*1 and ALDH2*1/ALDH2*2;
   ii) ADH2*1/ADH2*2 and ALDH2*1/ALDH2*2; or
   iii) ADH2*1/ADH2*2 and ALDH2*1/ALDH2*1.

* * * * *